(12) United States Patent
Viola

(10) Patent No.: US 8,091,756 B2
(45) Date of Patent: Jan. 10, 2012

(54) VARYING TISSUE COMPRESSION USING TAKE-UP COMPONENT

(75) Inventor: Frank Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 206 days.

(21) Appl. No.: 12/417,705

(22) Filed: Apr. 3, 2009

(65) Prior Publication Data

US 2009/0277947 A1    Nov. 12, 2009

Related U.S. Application Data

(60) Provisional application No. 61/051,907, filed on May 9, 2008.

(51) Int. Cl.
*A61B 17/072* (2006.01)

(52) U.S. Cl. .................. 227/178.1; 227/175.1; 227/19

(58) Field of Classification Search .... 227/175.1–182.1, 227/19
See application file for complete search history.

(56) References Cited

U.S. PATENT DOCUMENTS

| | | | |
|---|---|---|---|
| 1,756,670 A | 4/1930 | Treat | |
| 3,079,606 A * | 3/1963 | Bobrov et al. | 227/76 |
| 3,258,012 A | 6/1966 | Nakayama et al. | |
| 3,744,495 A | 7/1973 | Johnson | |
| 3,771,526 A | 11/1973 | Rudie | |
| 3,837,555 A | 9/1974 | Green | |
| 4,014,492 A | 3/1977 | Rothfuss | |
| 4,278,091 A | 7/1981 | Borzone | |
| 4,319,576 A | 3/1982 | Rothfuss | |
| 4,475,679 A | 10/1984 | Fleury, Jr. | |
| 4,527,437 A | 7/1985 | Wells | |
| 4,531,522 A | 7/1985 | Bedi et al. | |
| 4,532,927 A | 8/1985 | Miksza, Jr. | |
| 4,548,202 A | 10/1985 | Duncan | |
| 4,573,469 A | 3/1986 | Golden et al. | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,627,437 A | 12/1986 | Bedi et al. | |
| 4,741,336 A | 5/1988 | Failla et al. | |

(Continued)

FOREIGN PATENT DOCUMENTS

EP    0 129 442    12/1984

(Continued)

OTHER PUBLICATIONS

European Search Report for EP 09251268.0-2310 date of completion is Sep. 9, 2009 (3 pages).

(Continued)

*Primary Examiner* — Lindsay Low

(57) ABSTRACT

The present disclosure relates to surgical fastener applying apparatus, and the application of variable compression to tissue. More specifically, the presently disclosed surgical fastener applying apparatus act to limit the flow of blood through tissue immediately adjacent a cut-line formed therein to effectuate hemostasis, while maximizing the flow of blood through tissue more removed from the cut-line to limit unnecessary necrosis. In one embodiment, a surgical fastener applying apparatus is disclosed having a tool assembly coupled to a distal end thereof with first and second jaws respectively including an anvil and a surgical fastener cartridge. The surgical fastener cartridge includes, among other things, a hemostasis member that is configured to apply at least two different compressive forces to tissue clamped between the first and second jaws of the tool assembly.

18 Claims, 14 Drawing Sheets

U.S. PATENT DOCUMENTS

| | | |
|---|---|---|
| 4,767,044 A | 8/1988 | Green |
| 4,809,695 A | 3/1989 | Gwathmey et al. |
| 4,848,637 A | 7/1989 | Pruitt |
| 4,881,545 A | 11/1989 | Isaacs et al. |
| 4,930,503 A | 6/1990 | Pruitt |
| 4,941,623 A | 7/1990 | Pruitt |
| 4,978,049 A | 12/1990 | Green |
| 5,027,834 A | 7/1991 | Pruitt |
| 5,108,422 A | 4/1992 | Green et al. |
| 5,180,092 A | 1/1993 | Crainich |
| 5,201,746 A | 4/1993 | Shichman |
| 5,209,756 A | 5/1993 | Seedhom et al. |
| 5,219,353 A | 6/1993 | Garvey, III et al. |
| 5,240,163 A | 8/1993 | Stein et al. |
| 5,282,829 A | 2/1994 | Hermes |
| 5,342,396 A | 8/1994 | Cook |
| 5,350,400 A | 9/1994 | Esposito et al. |
| 5,352,229 A | 10/1994 | Goble et al. |
| 5,425,489 A | 6/1995 | Shichman et al. |
| 5,439,479 A | 8/1995 | Shichman et al. |
| 5,441,193 A | 8/1995 | Gravener |
| 5,452,836 A | 9/1995 | Huitema et al. |
| 5,452,837 A | 9/1995 | Williamson, IV et al. |
| 5,470,010 A | 11/1995 | Rothfuss et al. |
| 5,484,095 A | 1/1996 | Green et al. |
| 5,497,931 A | 3/1996 | Nakamura |
| 5,501,693 A | 3/1996 | Gravener |
| 5,509,920 A | 4/1996 | Phillips et al. |
| 5,551,622 A * | 9/1996 | Yoon .......................... 227/178.1 |
| 5,571,116 A | 11/1996 | Bolanos |
| 5,571,285 A | 11/1996 | Chow et al. |
| 5,584,856 A | 12/1996 | Jameel et al. |
| 5,620,452 A | 4/1997 | Yoon |
| 5,634,926 A | 6/1997 | Jobe |
| 5,667,526 A | 9/1997 | Levin |
| 5,667,527 A | 9/1997 | Cook |
| 5,676,674 A | 10/1997 | Bolanos et al. |
| 5,697,542 A | 12/1997 | Knodel et al. |
| 5,709,680 A | 1/1998 | Yates et al. |
| 5,741,268 A | 4/1998 | Schutz |
| 5,810,822 A | 9/1998 | Mortier |
| 5,865,361 A | 2/1999 | Milliman et al. |
| 5,871,135 A | 2/1999 | Williamson, IV et al. |
| 5,879,371 A | 3/1999 | Gardiner et al. |
| 5,915,616 A | 6/1999 | Viola et al. |
| 5,961,521 A | 10/1999 | Roger |
| 5,964,394 A | 10/1999 | Robertson |
| 6,083,242 A | 7/2000 | Cook |
| 6,202,914 B1 | 3/2001 | Geiste et al. |
| 6,273,897 B1 | 8/2001 | Dalessandro et al. |
| 6,325,810 B1 | 12/2001 | Hamilton et al. |
| 6,348,054 B1 | 2/2002 | Allen |
| 6,706,057 B1 | 3/2004 | Bidoia et al. |
| 6,786,382 B1 | 9/2004 | Hoffman |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,001,411 B1 | 2/2006 | Dean |
| 7,044,352 B2 | 5/2006 | Shelton, IV et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,398,908 B2 | 7/2008 | Holsten et al. |
| 7,455,676 B2 | 11/2008 | Holsten et al. |
| 7,472,815 B2 * | 1/2009 | Shelton et al. ............. 227/176.1 |
| 7,500,979 B2 | 3/2009 | Hueil et al. |
| 7,506,791 B2 * | 3/2009 | Omaits et al. ................ 227/177.1 |
| 7,604,151 B2 * | 10/2009 | Hess et al. .................. 227/181.1 |
| 7,669,746 B2 * | 3/2010 | Shelton, IV ................. 227/175.1 |
| 7,669,747 B2 * | 3/2010 | Weisenburgh et al. .... 227/180.1 |
| 7,708,180 B2 * | 5/2010 | Murray et al. .............. 227/175.1 |
| 7,744,627 B2 * | 6/2010 | Orban et al. .................. 606/215 |
| 2002/0042621 A1 | 4/2002 | Liddicoat et al. |
| 2004/0004105 A1 | 1/2004 | Jankowski |
| 2004/0073222 A1 | 4/2004 | Koseki |
| 2004/0093029 A1 | 5/2004 | Zubik et al. |
| 2004/0232195 A1 | 11/2004 | Shelton et al. |
| 2004/0232199 A1 | 11/2004 | Shelton et al. |
| 2004/0247415 A1 | 12/2004 | Mangone, Jr. |
| 2005/0006430 A1 | 1/2005 | Wales |
| 2005/0006431 A1 | 1/2005 | Shelton et al. |
| 2005/0006434 A1 | 1/2005 | Wales |
| 2005/0023324 A1 | 2/2005 | Doll et al. |
| 2005/0023325 A1 | 2/2005 | Gresham et al. |
| 2005/0059996 A1 | 3/2005 | Bauman et al. |
| 2005/0070925 A1 | 3/2005 | Shelton, IV et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2005/0263562 A1 | 12/2005 | Shelton, IV et al. |
| 2005/0267530 A1 | 12/2005 | Cummins |
| 2006/0000868 A1 | 1/2006 | Shelton, IV et al. |
| 2006/0015144 A1 | 1/2006 | Burbank et al. |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0025817 A1 | 2/2006 | Ortiz et al. |
| 2006/0039779 A1 | 2/2006 | Ring |
| 2006/0049230 A1 | 3/2006 | Shelton, IV et al. |
| 2006/0085030 A1 | 4/2006 | Bettuchi et al. |
| 2006/0097026 A1 | 5/2006 | Shelton, IV |
| 2006/0124688 A1 | 6/2006 | Racenet et al. |
| 2006/0163312 A1 | 7/2006 | Viola et al. |
| 2006/0226196 A1 | 10/2006 | Hueil et al. |
| 2006/0291981 A1 | 12/2006 | Viola et al. |
| 2007/0010838 A1 | 1/2007 | Shelton, IV et al. |
| 2007/0034667 A1 * | 2/2007 | Holsten et al. ............. 227/176.1 |
| 2007/0075115 A1 | 4/2007 | Olson et al. |
| 2007/0095877 A1 | 5/2007 | Racenet et al. |
| 2007/0131732 A1 * | 6/2007 | Holsten et al. ............. 227/179.1 |
| 2007/0262116 A1 | 11/2007 | Hueil et al. |
| 2008/0041918 A1 | 2/2008 | Holsten et al. |
| 2008/0078800 A1 | 4/2008 | Hess et al. |
| 2008/0078804 A1 | 4/2008 | Shelton et al. |

FOREIGN PATENT DOCUMENTS

| | | |
|---|---|---|
| EP | 0 169 044 | 1/1986 |
| EP | 0 588 081 | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1 607 048 | 12/2005 |
| EP | 1 728 473 | 12/2006 |
| EP | 1 754 445 A2 | 2/2007 |
| EP | 1 785 098 A2 | 5/2007 |
| EP | 1 875 868 | 1/2008 |
| EP | 1 917 918 | 5/2008 |
| EP | 1917918 A | 5/2008 |
| EP | 2 095 777 | 9/2009 |
| FR | 2838952 | 10/2003 |
| GB | 2 019 296 | 10/1979 |
| GB | 2 029 754 | 3/1980 |
| GB | 2 051 287 | 1/1981 |
| SU | 405234 | 9/1975 |
| SU | 1333319 | 8/1987 |
| SU | 1442191 | 12/1988 |
| SU | 1459659 | 2/1989 |
| WO | WO 86/02254 A1 | 4/1986 |
| WO | WO 90/05489 | 5/1990 |
| WO | WO 96/19146 | 6/1996 |
| WO | WO 97/34533 | 9/1997 |
| WO | WO 02/30296 | 4/2002 |
| WO | WO 03/094743 | 11/2003 |
| WO | WO 03/094747 | 11/2003 |

| WO | WO 2006/055385 | 5/2006 |
| WO | WO 2008/007377 | 1/2008 |
| WO | WO 2008/039250 | 4/2008 |
| WO | WO2008/089050 | 7/2008 |

OTHER PUBLICATIONS

European Search Report for EP 06016963.8-2318 date of completion is Mar. 9, 2007.
European Search Report dated Jan. 31, 2011 for European Patent Appln. No. EP 10 25 1797.
International Search Report from EP Application No. 07 25 4366 dated Nov. 11, 2010.
International Search Report from EP Application No. 09 25 1067 mailed Mar. 17, 2011.
European Search Report EP08 25 2283 dated Jan. 15, 2009.
European Search Report EP09 25 1793 dated Nov. 3, 2009.
European Search Report EP09 25 1268 dated Sep. 9, 2009.
European Search Report EP09 25 1240 dated Oct. 5, 2009.
European Search Report EP11 00 4299 dated Aug. 2, 2011.

* cited by examiner

VARYING TISSUE COMPRESSION USING TAKE-UP COMPONENT

CROSS-REFERENCE TO RELATED APPLICATIONS

This application claims the benefit of, and priority to, U.S. Provisional Pat. Application Ser. No. 61/051,907, filed on May 9, 2008, the entire contents of which are incorporated by reference herein.

BACKGROUND

1. Technical Field

The present disclosure relates to surgical fastener applying apparatus. More particularly, the present disclosure relates to a tool assembly for use with a surgical fastener applying apparatus, and methods of using and manufacturing the same, to apply a plurality of surgical fasteners to tissue with varying compressive forces. The present disclosure also relates to hemostasis members, and accessories used in applying surgical fasteners, to support tissue being joined, aid in providing hemostasis of joined tissues, and/or promote healing.

2. Background of the Related Art

Many varieties of surgical fastener applying apparatus are known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. Suitable examples of apparatus which may be used during the course of these procedures can be seen in U.S. Pat. Nos. 5,915,616; 6,202,914; 5,865,361; and 5,964,394. 5,915,616

In general, a surgical fastener applying apparatus will include an anvil that is approximated relative to a surgical fastener cartridge during use. The anvil includes depressions that are aligned with, and/or are in registration with slots defined in the surgical fastener cartridge, through which the fasteners will emerge. To effectuate formation, the fasteners emerge from the surgical fastener cartridge and are driven against the anvil. Certain surgical fastener cartridges have one or more rows of fasteners disposed laterally outward of a slot that is configured to accommodate a knife, or other such cutting element, such that tissue can be simultaneously severed and joined together at a cut-line. Depending upon the particular surgical fastener applying apparatus, the rows of fasteners may be arranged in a linear, non-linear, e.g. circular, semi-circular, or other configuration.

Various types of surgical fasteners are well known in the art including, but not limited to, unitary fasteners and two-part fasteners. Unitary fasteners generally include a pair of legs that are adapted to penetrate tissue and connected by a backspan from which they extend. In use, subsequent to formation, certain types of unitary fasteners have a "B" shaped configuration. Typically, the two-part fastener includes legs that are barbed and connected by a backspan. The legs are engaged and locked into a separate retainer piece that is usually located in the anvil. In use, the two-part fastener is pressed into the tissue so that the barbs penetrate the tissue and emerge from the other side where they are then locked into the retainer piece. The retainers prevent the two-part fastener from dislodging from the tissue. The two-part fasteners are not intended to be unlocked or removable. They are generally made of a bioabsorbable material.

A common concern in each of the procedures mentioned above is hemostasis, or the cessation of bleeding of the target tissue. It is commonly known that by increasing the amount of pressure applied to a wound, the flow of blood can be limited, thereby decreasing the time necessary to achieve hemostasis. To this end, conventional surgical fastener applying apparatus generally apply two or more rows of fasteners about the cut-line to compress the surrounding tissue in an effort to stop any bleeding and to join the cut tissue together. Each of the fasteners will generally apply a compressive force to the tissue sufficient to effectuate hemostasis. However, applying too much pressure can result in a needless reduction in blood flow to the tissue surrounding the cut-line, resulting in an elevated level of necrosis, a slower rate of healing, and/or a greater recovery period.

Consequently, it would be advantageous to provide a surgical fastener applying apparatus capable of limiting the flow of blood in the tissue immediately adjacent the cut-line to effectuate hemostasis and wound closure, while maximizing blood flow in the surrounding tissue to facilitate healing. Additionally, when tissue is clamped and compressed between the anvil and the surgical fastener cartridge, some of the fluid retained within the tissue is squeezed out, which results in greater compression at the portions of the surgical fastener cartridge and the anvil adjacent the cut-line when compared to the lateral edges. It may also be desirable to cut and fasten across tissue that varies in thickness. It would be advantageous to fasten tissue in a manner that applies variable compressive forces to tissue.

SUMMARY

The present disclosure relates to surgical fastener applying apparatus that apply variable compression to tissue, and/or accommodate tissue of varying thickness. More specifically, surgical fastener applying apparatus in accordance with the principles of the present disclosure act to limit the flow of blood through tissue immediately adjacent a cut-line formed therein to effectuate hemostasis, while maximizing the flow of blood through tissue more removed from the cut-line to limit unnecessary necrosis.

In one aspect of the present disclosure, a surgical fastener applying apparatus is disclosed that includes a first jaw having proximal and distal ends and an anvil member extending along a longitudinal axis and including a tissue contacting surface, a second jaw having proximal and distal ends that is movably coupled to the first jaw and including a surgical fastener cartridge, or cartridge member, and a hemostasis member that is positioned between the first jaw and the second jaw.

The hemostasis member may be formed of a substantially resilient material to support layers of tissue positioned between the first and second jaws, and may be either fixedly or releasably secured to the cartridge member.

The hemostasis member includes a stepped profile that is configured and dimensioned to apply at least two different compressive forces to tissue during approximation of the first and second jaws. The hemostasis member may be configured and dimensioned such that the compressive forces applied to the tissue are varied along an axis that is transverse to the longitudinal axis. Additionally, or alternatively, the hemostasis member may be configured and dimensioned such that the compressive forces applied to the tissue decrease outwardly relative to a centerline of the cartridge member such that blood flow through the tissue nearer to the centerline of the cartridge member is less than blood flow through the tissue further from the centerline of the cartridge member. It is also envisioned that the hemostasis member may be configured and dimensioned such that the compressive forces applied to the tissue are varied along the longitudinal axis. For example, the hemostasis member may be configured and dimensioned such that the compressive forces applied to the tissue decrease in a proximal direction along the longitudinal axis such that blood flow through the tissue nearer to the distal ends of the anvil member and the cartridge member is less than blood flow through the tissue nearer to the proximal ends of the anvil member and the cartridge member. Alternatively, the hemostasis member may be configured and dimensioned such that the compressive forces applied to the tissue decrease in a distal direction along the longitudinal axis such that blood flow through tissue nearer to the proximal ends of the anvil member and the cartridge member is less than blood flow through tissue nearer to the distal ends of the anvil member and the cartridge member.

The stepped profile of the hemostasis member defines a first tissue contacting surface and a second tissue contacting surface, wherein the second tissue contacting surface is positioned outwardly of the first tissue contacting surface relative to the longitudinal axis. The first tissue contacting surface defines a first gap with the tissue contacting surface of the anvil member, and the second tissue contacting surface defines a second, larger gap with the tissue contacting surface of the anvil member. The first and second tissue contacting surfaces may be generally planar in configuration, and the first tissue contacting surface is connected to the second tissue contacting surface via a first wall surface with a generally tapered configuration.

In one embodiment of the hemostasis member, the stepped profile thereof may further define a third tissue contacting surface that is positioned outwardly of the second tissue contacting surface relative to the longitudinal axis. The third tissue contacting surface defines a third gap with the tissue contacting surface of the anvil member that is larger than the second gap. In this embodiment, the second tissue contacting surface is connected to the third tissue contacting surface via a second wall surface with a generally tapered configuration.

The surgical fastener applying apparatus may further include a plurality of surgical fasteners that are positioned within the cartridge member, each of which defines a substantially equivalent height.

In another aspect of the present disclosure, a hemostasis member is disclosed for use with a surgical fastener applying apparatus including an anvil member and a cartridge member having a plurality of surgical fasteners arranged in at least one row. The disclosed hemostasis member is shaped and configured to overlie the at least one row of surgical fasteners, and includes a profile shaped, configured, and dimensioned to apply at least two different compressive forces to tissue during approximation of the anvil member and the cartridge member.

In one embodiment, the hemostasis member is configured and dimensioned such that the compressive forces are varied along an axis transverse to the longitudinal axis along which the anvil and cartridge members of the surgical fastener applying apparatus extend. Specifically, the hemostasis member may be configured and dimensioned such that the compressive forces applied to the tissue decrease outwardly relative to a centerline of the cartridge member such that blood flow through the tissue nearer to the centerline of the cartridge member is less than blood flow through the tissue further from the centerline of the cartridge member.

In an alternative embodiment, it is envisioned that the hemostasis member may be configured and dimensioned such that the compressive forces are varied along the longitudinal axis.

It is also envisioned that the surgical fastener applying apparatus may extend along a longitudinal axis, but that the anvil and cartridge members may be arcuate in shape, extending transversely to the longitudinal axis. In this embodiment, the hemostasis member may be configured and dimensioned such that the compressive force is varied along an axis transverse to the longitudinal axis.

These and other features of the surgical access apparatus and hemostasis member disclosed herein will become more readily apparent to those skilled in the art through reference to the detailed description of various embodiments of the present disclosure that follows.

BRIEF DESCRIPTION OF THE DRAWINGS

Various embodiments of the present disclosure are described herein below with references to the drawings, wherein.

DETAILED DESCRIPTION OF THE EMBODIMENTS

Figure 1:
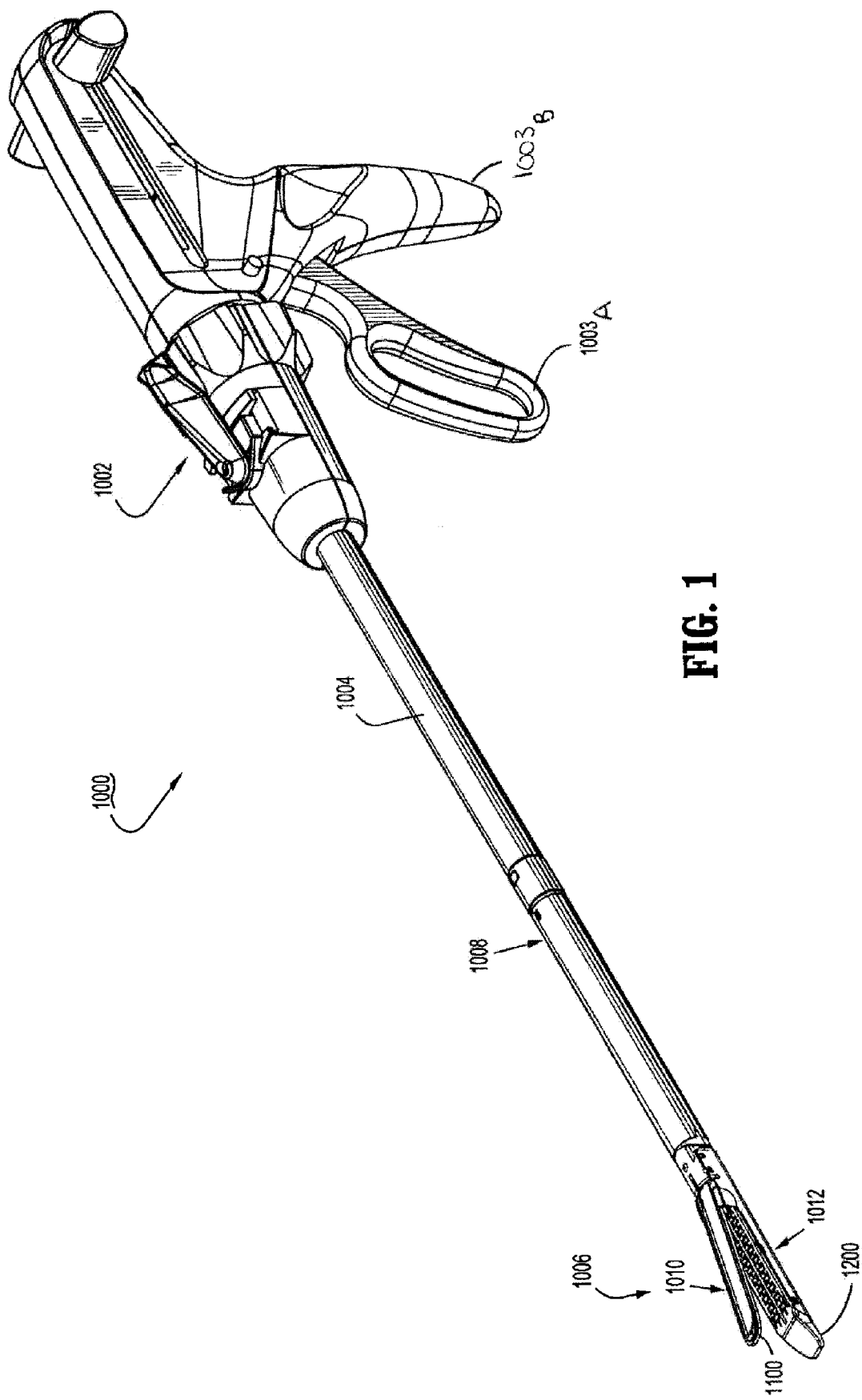
FIG. 1 is a top, perspective view of a surgical fastener applying apparatus having a tool assembly at a distal end thereof for applying a plurality of surgical fasteners to tissue, according to one embodiment of the present disclosure.

Various embodiments of the presently disclosed surgical fastener applying apparatus, and methods of using the same, will now be described in detail with reference to the drawings wherein like references numerals identify similar or identical elements. In the drawings, and in the description which follows, the term "proximal" will refer to the end the surgical fastener applying apparatus, or component thereof, that is closer to the operator during use, while the term "distal" will refer to the end that is further from the operator, as is traditional and conventional in the art. In addition, the term "surgical fastener" should be understood to include any substantially rigid structure formed of a biocompatible material that is suitable for the intended purpose of joining tissue together, including but not being limited to surgical staples, clips, and the like.

FIG. 1 illustrates a surgical fastener applying apparatus 1000, of either the re-usable or disposable variety, including a handle assembly 1002 with a movable handle $1003_A$ and a stationary handle $1003_B$, an elongated shaft 1004 extending distally from the handle assembly 1002, and a tool assembly 1006 that is coupled to a distal end 1008 of the elongated shaft 1004. In various embodiments, it is envisioned that the handle assembly 1002 may include motor-driven, hydraulic, ratcheting, or other such mechanisms. In general, the tool assembly 1006 is adapted to clamp, fasten together, and sever adjacent tissue segments along a cut-line. During use, the surgical fastener applying apparatus 1000 is approximated and fired similarly to, and in accordance with other known surgical fastener applying apparatus. A discussion of the approximation and firing of surgical fastener applying apparatus 1000, including the components and interaction of the handle assembly 1002 and included drive assembly, is provided below. Additional details of the approximation and firing of surgical fastener applying apparatus 1000 may also be obtained through reference to commonly assigned U.S. Pat. No. 5,865,361, currently assigned to Tyco Healthcare Group LP, the contents of which are hereby incorporated by reference herein in its entirety.

Referring now to FIGS. 2-6 as well, the tool assembly 1006 includes a first jaw 1010 that is pivotally coupled to a second jaw 1012 to facilitate approximation thereof. The first jaw 1010 of the tool assembly 1006 includes an anvil 1100, and the second jaw 1012 includes a surgical fastener cartridge 1200 that is loaded with a plurality of surgical fasteners 100. Pivoting the movable handle $1003_A$ towards the stationary handle $1003_B$ (FIG. 1) approximates the first jaw 1010 towards the second jaw 1012. After the jaws 1010, 1012 are in close operative alignment, continued pivoting of the movable handle $1003_A$ ejects the plurality of surgical fasteners 100 from the surgical fastener cartridge 1200 such that the plurality of surgical fasteners 100 are driven into the anvil 1100, thus being formed into completed surgical fasteners, as described in further detail below. The cartridge 1200 in certain embodiments is removable and replaceable with another loaded cartridge. In other embodiments, the tool assembly 1006 comprises or forms a part of a removable and replaceable loading unit for the surgical fastener applying apparatus 1000. Further details regarding ejection of the surgical fasteners 100 is provided below.

Figure 2:
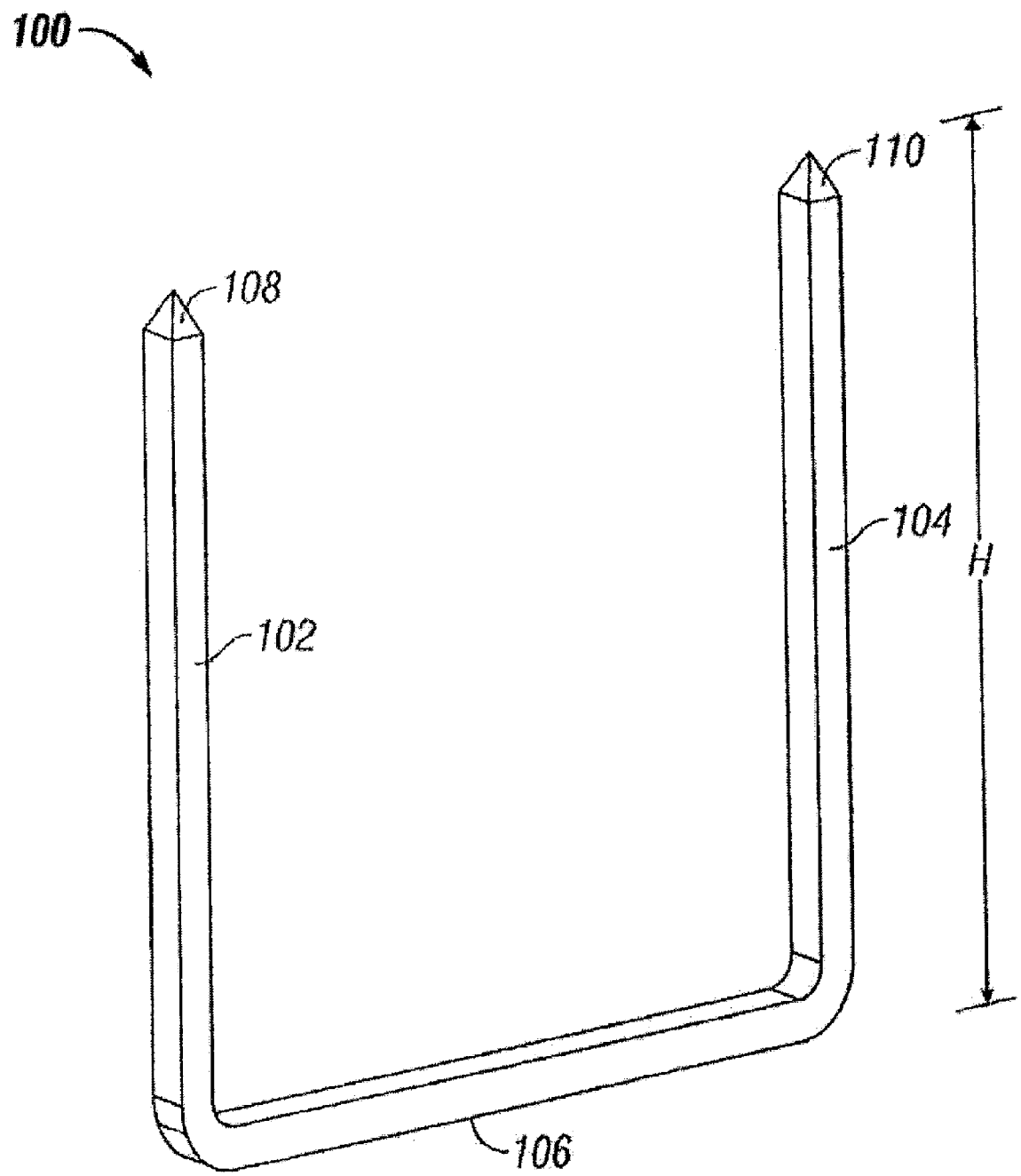
FIG. 2 is a side, perspective view of a surgical fastener according to the present disclosure.

Each surgical fastener 100 includes two legs 102, 104 that are connected by a backspan 106 extending therebetween (FIG. 2). The legs 102, 104 extend from the backspan 106 to respective penetrating ends 108, 110 such that each surgical fastener 100 defines a substantially equivalent height "H" prior to formation. The dimensions of the backspan 106 and the legs 102, 104 can be varied such that the surgical fastener 100 may be used to fasten tissue having varying attributes, such as the thickness thereof or the presence of scar tissue.

The legs 102, 104 and the backspan 106 may define a cross-section having any suitable geometric configuration including, but not limited to, rectangular, oval, square, triangular, trapezoidal, etc. The legs 102, 104 and the backspan 106 may exhibit the same geometrical configuration, as shown in FIG. 2, or alternatively, the legs 102, 104 and the backspan 106 may exhibit different geometrical configurations. For example, the legs 102, 104 may exhibit a rectangular cross-section, whereas the backspan 106 may exhibit an oval cross-section.

The respective penetrating ends 108, 110 of the legs 102, 104 may be tapered to facilitate the penetration of tissue, or alternatively, the penetrating ends 108, 110 may not include a taper. In various embodiments, it is also envisioned that the penetrating ends 108, 110 may define either a conical surface, or flat surface.

Prior to formation, the legs 102, 104 of each surgical fastener 100 may extend from the backspan 106 such that they are substantially parallel. In the alternative, the legs 102, 104 may converge or diverge from the backspan 106.

Figure 3:
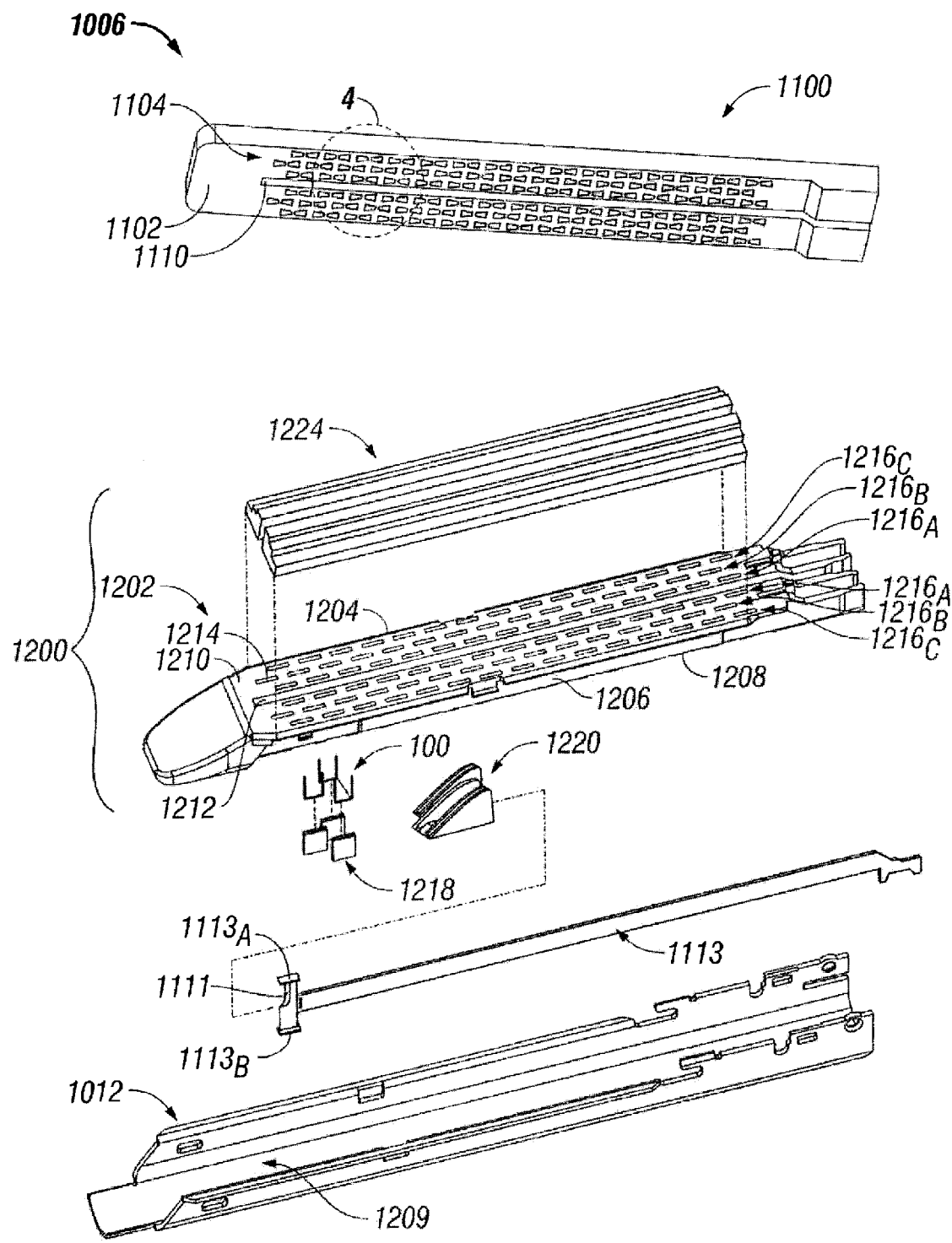
FIG. 3 is a partial perspective view of the tool assembly seen in FIG. 1 with parts separated illustrating an anvil and a surgical fastener cartridge including a hemostasis member having a stepped configuration.
Figure 4:
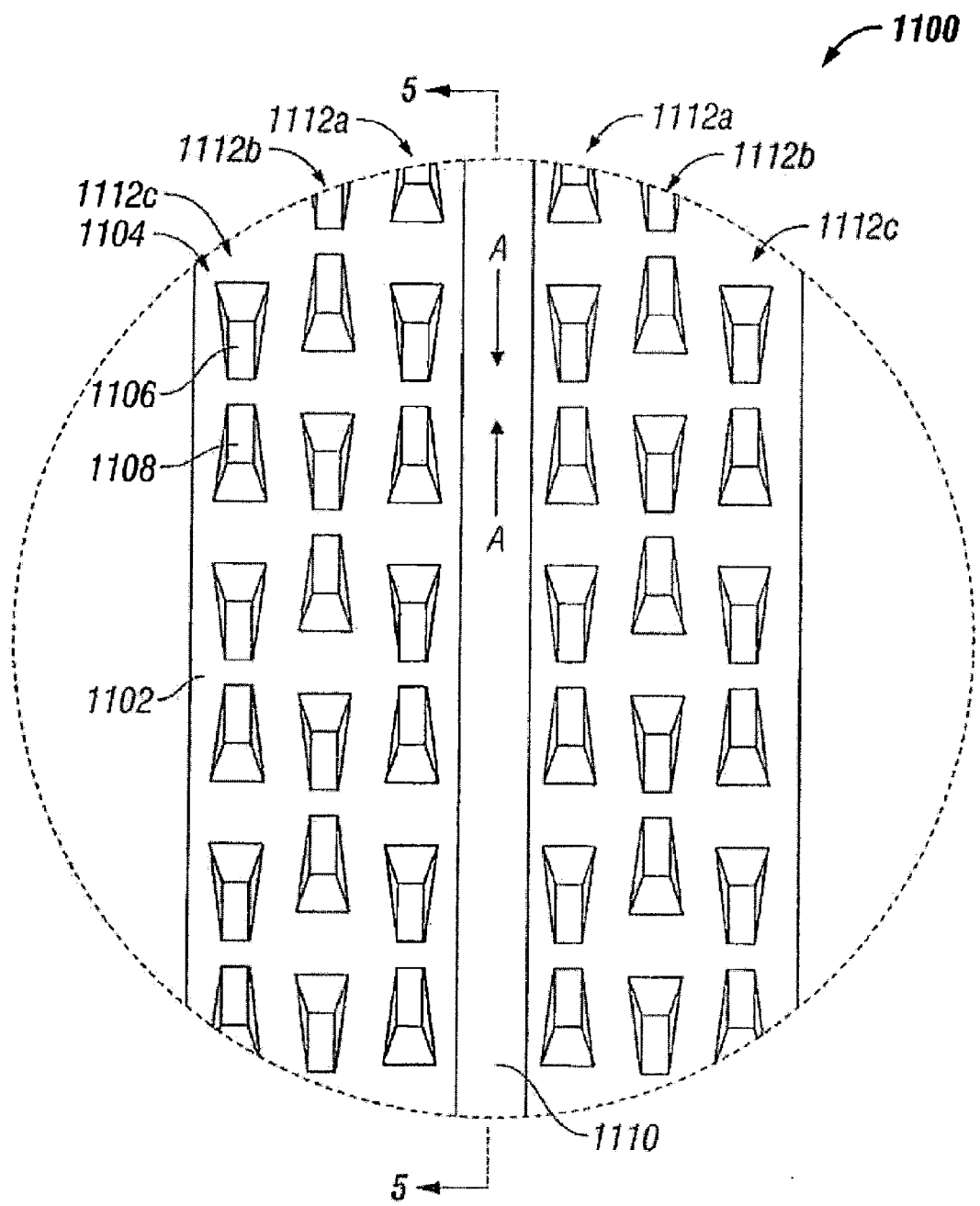
FIG. 4 is a schematic, enlarged view of the area of detail indicated in FIG. 3 illustrating a tissue contacting surface of the anvil and a plurality of pockets formed therein.
Figure 5:
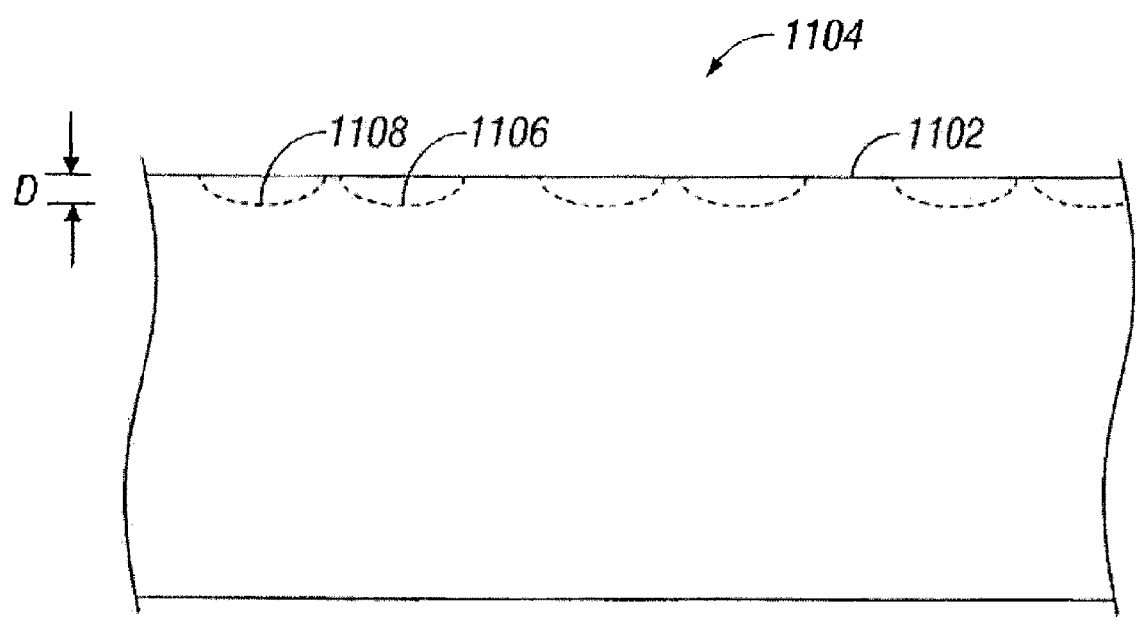
FIG. 5 is a longitudinal, cross-sectional view taken along line 5-5 in FIG. 4 illustrating the pockets formed in the tissue contacting surface of the anvil.
Figure 7:
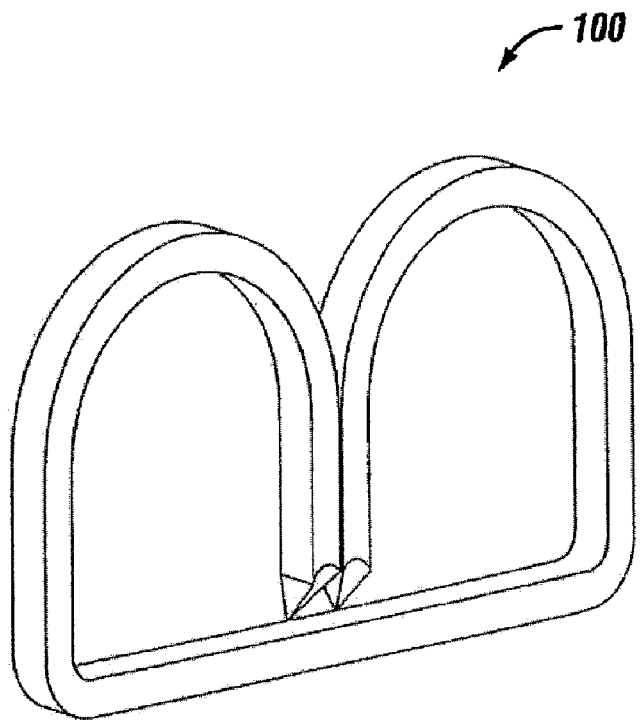
FIG. 7 is a side, perspective view of the surgical fastener shown in FIG. 2 exhibiting a standard "B" shaped configuration subsequent to formation through engagement with the pockets formed in the anvil seen in FIG. 3.
Figure 8:
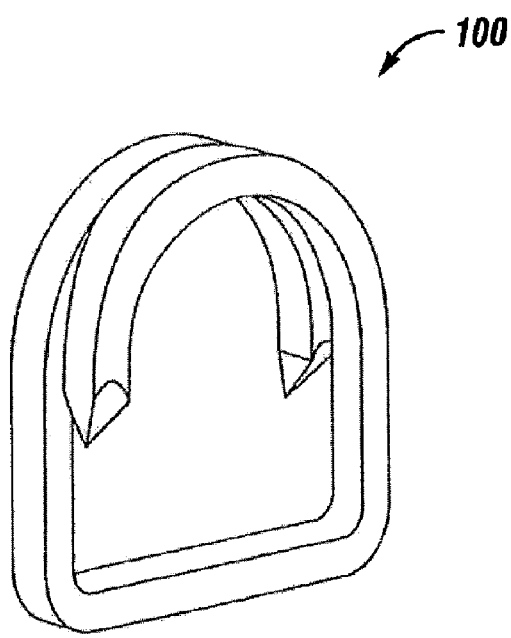
FIG. 8 is side, perspective view of a surgical fastener having a single-loop configuration subsequent to formation through contact with the pockets formed in the tissue contacting surface of an alternative embodiment of the anvil seen in FIG. 3.

With reference now to FIGS. 3-5 in particular, the anvil 1100 will be discussed. The anvil 1100 is an elongated member having a tissue contacting surface 1102 with a plurality of pockets 1104 formed therein. Each of the pockets 1104 is positioned to receive and deform the legs 102, 104 of a surgical fastener 100 to achieve a formed configuration. More particularly, each pocket 1104 formed in the anvil 1100 includes two forming surfaces 1106, 1108 that extend into the anvil 1100, i.e., away from the tissue contacting surface 1102, to define a depth "D", as best seen in FIG. 5. Upon engagement of the legs 102, 104 with the forming surfaces 1106, 1108, the forming surfaces 1106, 1108 guide the legs 102, 104 inwardly in the direction of arrows "A" (FIG. 4) to facilitate deformation of the surgical fastener 100 into a standard "B" shaped configuration (FIG. 7). In an alternative embodiment, the anvil 1100 may include pockets 1104 that are configured and dimensioned to deform the surgical fastener 100 such that the fastener 100 defines a single-loop configuration (FIG. 8) upon formation. It is also envisioned that the surgical fasteners 100 may exhibit other configurations upon formation.

The pockets 1104 are arranged into rows disposed on opposite sides of a slot 1110 extending through the anvil 1100 (FIGS. 3, 4). The slot 1110 is configured to accommodate movement of a knife 1111, or other such cutting element, such that tissue may be severed along a cut-line. Although the slot 1110 is depicted as extending longitudinally through the anvil 1100, in alternative embodiments, the slot 1110 may define a configuration that is angled, arcuate, or shaped otherwise. The slot 1110 may extend along a centerline of the anvil 1100, as shown in the embodiment illustrated in FIGS. 3 and 4, or alternatively, the slot 1110 may be offset from the centerline of the anvil 1100.

The anvil 1100 includes a pair of inner rows $1112_A$, a pair of intermediate rows $1112_B$, and a pair of outer rows $1112_C$ (FIG. 4) The inner pair of rows $1112_A$ are spaced laterally outward of the slot 1110 and are closest thereto, the pair of intermediate rows $1112_B$ are spaced laterally outward from the pair of inner rows $1112_A$, and the pair of outer rows $1112_C$ are spaced laterally outward from the pair of intermediate rows $1112_B$ and are furthest from the slot 1110. While the anvil 1100 is depicted as including three pairs of rows, i.e., the respective pairs of inner, intermediate, and outer rows $1112_A$, $1112_B$, $1112_C$, fewer and greater numbers of rows of pockets 1104 may be included in alternative embodiments of the anvil 1100.

With continued reference to FIGS. 3-5, the surgical fastener cartridge 1200 will be described. The surgical fastener cartridge 1200 includes a cartridge body 1202 with a pair of side walls 1204, 1206, a bottom wall 1208, and a top wall 1210 (FIG. 3), and resides in a channel 1209 defined by the second jaw 1012. The cartridge body 1202 includes a slot 1212 extending therethrough that is configured to accommodate longitudinal movement of the knife 1111 (FIG. 3). As discussed above with respect to the anvil 1100, while the slot 1212 is depicted as extending longitudinally through the surgical fastener cartridge 1200, in alternative embodiments, the slot 1212 may define a configuration that is angled, arcuate, or shaped otherwise. The slot 1212 is arranged to correspond with the slot in the anvil 1100. The slot 1212 may extend along a centerline of the surgical fastener cartridge 1200, as shown in the embodiment illustrated in FIG. 3, or alternatively, the slot 1212 may be spaced therefrom.

The top wall 1210 of the cartridge body 1202 includes a plurality of retention slots 1214 (FIG. 3) formed therein that are arranged into rows corresponding in position to the rows of pockets 1104 (FIG. 4) formed in the tissue contacting surface 1102 of the anvil 1100. Accordingly, in the particular embodiment of the surgical fastener cartridge 1200 seen in FIG. 3, the top wall 1210 is substantially planar and parallel to the tissue contacting surface 1102 of the anvil. Also in FIG. 3, the retention slots 1214 are arranged into a pair of inner rows $1216_A$, a pair of intermediate rows $1216_B$, and a pair of outer rows $1216_C$, each of which is disposed on opposite sides of the slot 1212. The pair of inner rows $1216_A$ are spaced laterally outward of the slot 1212 and are closest thereto, the pair of intermediate rows $1216_B$ are spaced laterally outward from the pair of inner rows $1216_A$, and the pair of outer rows $1216_C$ are spaced laterally outward from the pair of intermediate rows $1216_B$ and are furthest from the slot 1212. While the surgical fastener cartridge 1200 is depicted as including three pairs of rows, i.e., the respective inner, intermediate, and outer rows $1216_A$, $1216_B$, $1216_C$, fewer and greater numbers of rows of fastener retention slots 1214 may be included in alternative embodiments of the surgical fastener cartridge 1200. In certain embodiments, the surgical fastener cartridge does not include a slot for accommodating a knife.

Figure 9:
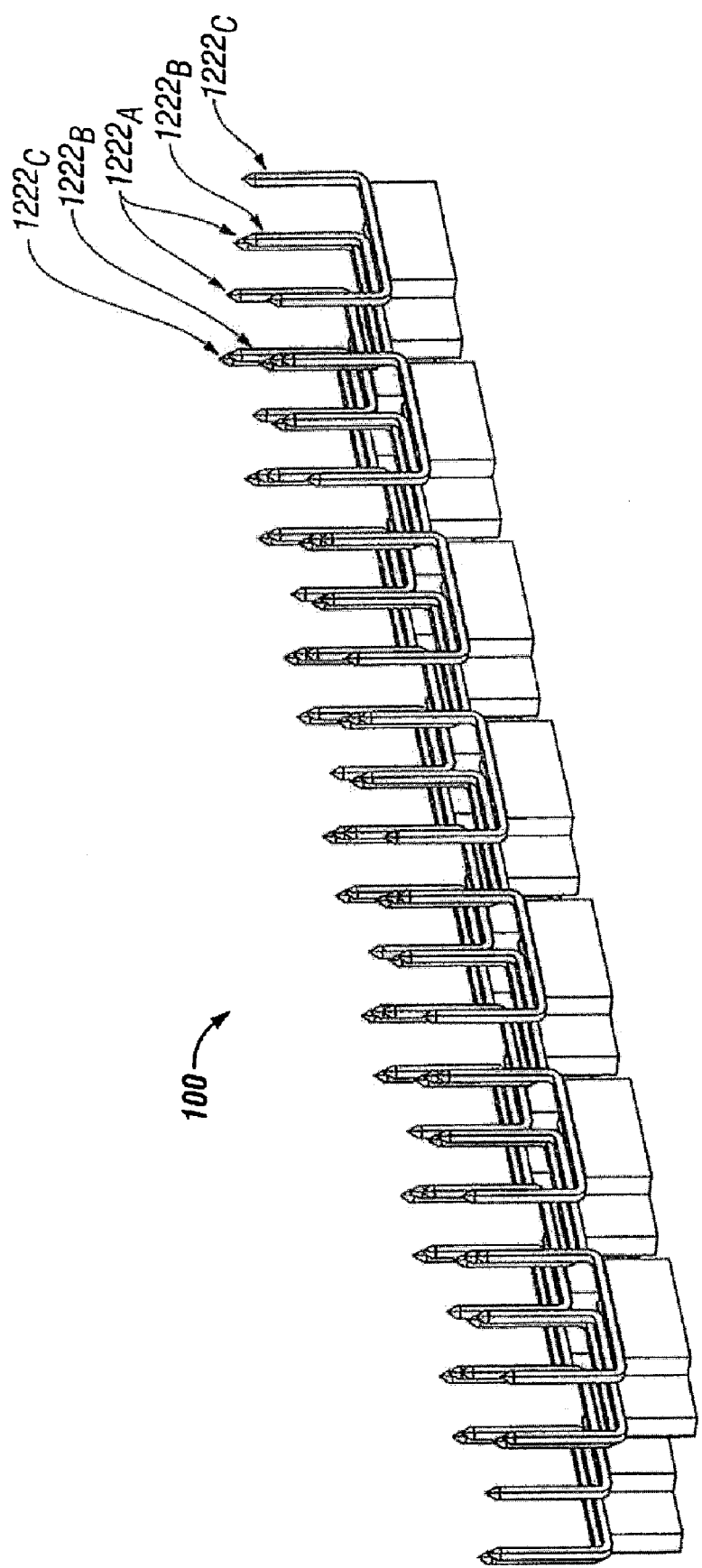
FIG. 9 is a partial longitudinal, perspective view, with parts removed, of the surgical fastener cartridge seen in FIG. 3 illustrating the plurality of surgical fasteners arranged into inner, intermediate, and outer rows.

Each fastener retention slot 1214 is configured and dimensioned to receive a surgical fastener 100 (FIG. 3), as well as a correspondingly dimensioned pusher 1218 positioned therein. The pusher 1218 and the surgical fastener 100 are driven upwardly, i.e. towards the top wall 1210, by a sled 1220 (FIG. 3), as discussed in further detail below. As the surgical fasteners 100 exit the fastener retention slots 1214, they are necessarily deployed in rows, i.e., respective inner, intermediate, and outer rows $1222_A$, $1222_B$, $1222_C$ (FIG. 9), on opposite sides of the cut-line created in the tissue.

Referring now to FIGS. 3-6, the surgical fastener cartridge 1200 further includes a hemostasis member 1224 that is configured and dimensioned to apply a variable compressive force to tissue positioned between the jaws 1010, 1012 (FIG. 1) of the tool assembly 1006. In the embodiment of the hemostasis member 1224 seen in FIGS. 3 and 6, the hemostasis member 1224 is configured as a pad, through which the slot 1212 also extends. The hemostasis member 1224 is attached to, or otherwise disposed on, the top wall 1210, and may be fixedly or releasably attached thereto in alternative embodiments. In those embodiments wherein the hemostasis member 1224 is releasably connected to the top wall 1210, it is envisioned that the hemostasis member 1224 seen in FIGS. 3 and 6 may be selectively replaced with one of the alternative embodiments discussed herein below.

The hemostasis member 1224 may be formed from any suitable biocompatible material that is sufficiently resilient to support layers of tissue while permitting the plurality of surgical fasteners 100 to pass therethrough during formation. The hemostasis member 1224 may be formed of organic or synthetic tissue, and may be configured and dimensioned to provide support to and/or to reinforce tissue about the cut-line. The hemostasis member 1224 may comprise a buttress, fastener line reinforcement material, pledget, or other such materials. The hemostasis member may be a bio-absorbable or non-absorbable material suitable for implantation in the body and configured as a mesh, pad of material, composite materials, materials including fibers, collagen or other materials derived from natural tissue, and other materials for surgical implantation. The hemostasis member may comprise a known surgical stapling buttress, pledget, or tissue support, and may be formed from, or include, a hemostat, medicament, coagulant, adhesive, or sealant. The materials described in U.S. Patent Application Publication No. 2007-0203510 A1, published Aug. 30, 2007, the disclosure of which is hereby incorporated by reference herein, may be used to form the hemostasis member.

Figure 6:
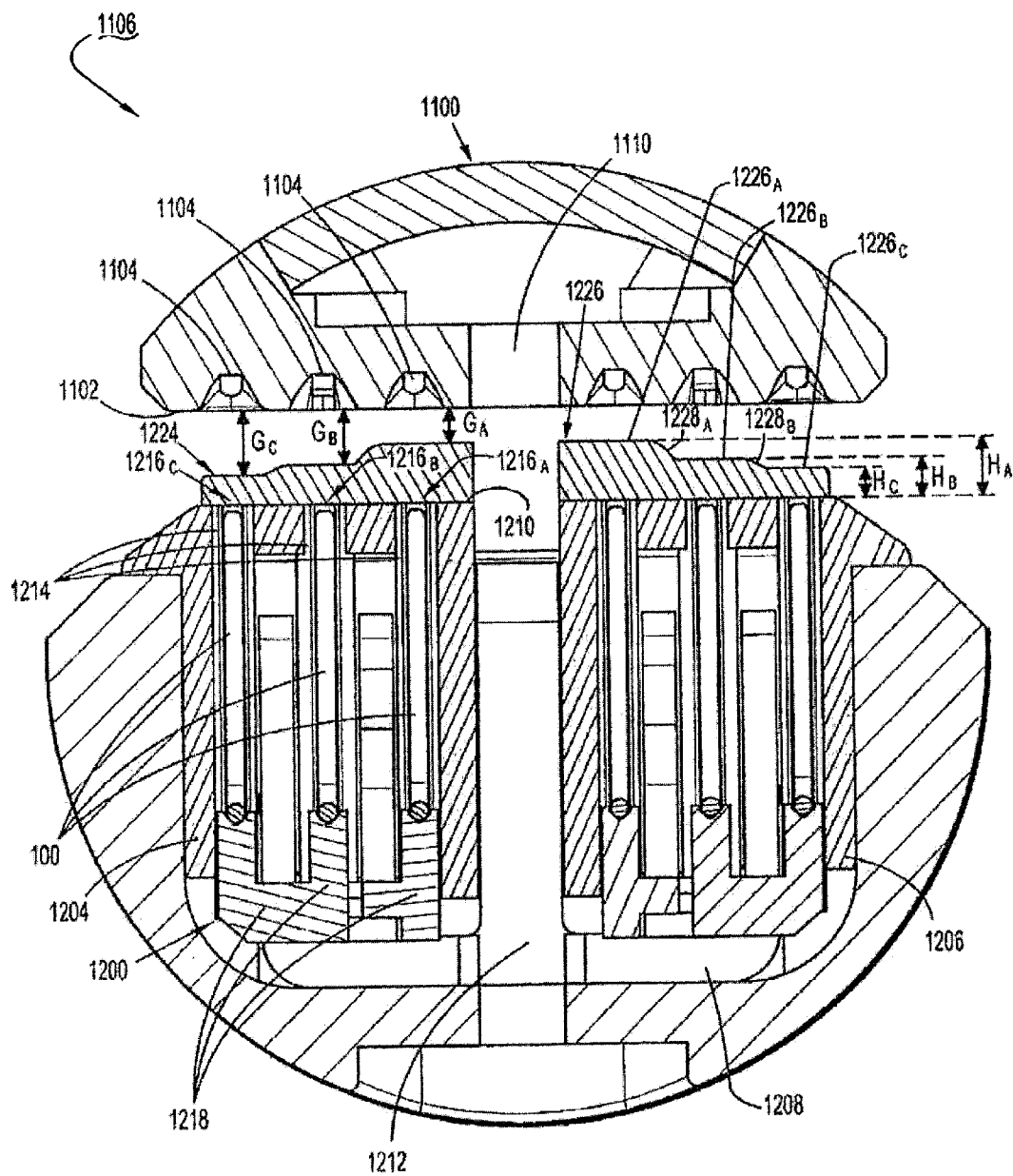
FIG. 6 is a lateral, cross-sectional view of the tool assembly seen in FIG. 1 taken through the pockets formed in the anvil and retention slots formed in the surgical fastener cartridge.

The configuration of the hemostasis member applies different pressure to tissue, depending upon the location of the tissue with respect to the hemostasis member. The configuration and dimensions of the hemostasis member 1224 in FIGS. 3 and 6 are intended to improve the degree of hemostasis achieved at the cut-line when layers of tissue are joined using the tool assembly 1006. In the embodiment of the hemostasis member 1224 seen in FIGS. 3 and 6, the configuration and dimensions of the hemostasis member 1224 facilitate the application of a compressive force to the tissue that is gradually decreased as the lateral distance from the cut-line is increased. Accordingly, upon approximation of the respective first and second jaws 1010, 1012 of the tool assembly 1006 (FIG. 1), the flow of blood through the tissue immediately adjacent and surrounding the cut-line will be substantially less than the flow of blood through the tissue spaced laterally therefrom. Alternatively, or additionally, the hemostasis member 1224 may take up space between the backspan 106 (FIG. 2) of the fastener 100 and the tissue such as, for example, in areas of relatively thin tissue.

The hemostasis member 1224 includes a tissue contacting surface 1226, e.g., for maintaining the position of the tissue to be cut. In the embodiment of the hemostasis member 1224 seen in FIGS. 3 and 6, the tissue contacting surface 1226 defines three discrete tissue contacting surfaces, i.e., an inner tissue contacting surface $1226_A$, an intermediate tissue contacting surface $1226_B$, and an outer tissue contacting surface $1226_C$. However, in alternative embodiments, the hemostasis member 1224 may define fewer or additional numbers of tissue contacting surfaces.

The respective inner, intermediate, and outer tissue contacting surfaces $1226_A$, $1226_B$, $1226_C$ extend in substantially parallel relation, and are each substantially planar in configuration. A first wall surface $1228_A$ interconnects the tissue contacting surfaces $1226_A$ and $1226_B$, and a second wall surface $1228_B$ interconnects the tissue contacting surfaces $1226_B$ and $1226_C$. As shown, the respective first and second wall surfaces $1228_A$, $1228_B$ are sloping with respect to the tissue contacting surfaces $11226_A$, $1226_B$ and $1226_C$ so that the hemostasis member generally tapers toward the outer edges of the hemostasis member and is generally stepped in configuration. The respective first and second wall surfaces $1228_A$, $1228_B$ are curved in FIG. 6. However, in other embodiments, the first and second wall surfaces may be generally planar in configuration.

Each of the tissue contacting surfaces $1226_A$, $1226_B$, $1226_C$ defines a different height measured from the top wall 1210 of the surgical fastener cartridge 1200 such that the hemostasis member 1224 defines a stepped configuration or profile. Consequently, each tissue contacting surface $1226_A$, $1226_B$, $1226_C$ defines a different corresponding tissue gap measured with the tissue contacting surface 1102 of the anvil 1100. Specifically, the inner tissue contacting surface $1226_A$ defines a first height "$H_A$" and a corresponding first tissue gap "$G_A$," the intermediate tissue contacting surface $1226_B$ defines a second height "$H_B$" and a corresponding second tissue gap "$G_B$," and the outer tissue contacting surface $1226_C$ defines a third height "$H_C$" and a corresponding third tissue gap "$G_C$." In the embodiment of the hemostasis member 1224 seen in FIGS. 3 and 6, the first height "$H_A$" is greater than the second height "$H_B$" and the second height "$H_B$" is greater than the third height "$H_C$" such that the first tissue gap "$G_A$" is less than the second tissue gap "$G_B$" and the second tissue gap "$G_B$" is less than the third tissue gap "$G_C$." In alternative embodiments, however, the respective first, second, and third heights "$H_A$," "$H_B$," "$H_C$" may be varied to define any desired tissue gap, and accordingly, to apply the compressive force necessary to achieve any desired measure of hemostasis.

By including a stepped configuration, the hemostasis member 1224 is able to achieve a particular degree of compression that can be varied with the distance from the cut-line in any desired manner. For example, if a gradual decrease in compression is desired, the heights "$H_A$," "$H_B$," "$H_C$" of each tissue contacting surface $1226_A$, $1226_B$, $1226_C$ can be reduced steadily, e.g., in a linear fashion. However, if a more dramatic compression gradient is desired, the heights "$H_A$," "$H_B$," "$H_C$" of each tissue contacting surface $1226_A$, $1226_B$, $1226_C$ can be reduced more dramatically. For example, the height "$H_A$" of the tissue contacting surface $1226_A$ may be significantly greater than the respective heights "$H_B$," "$H_C$" of the tissue contacting surfaces $1226_B$, $1226_C$.

In alternative embodiments, the hemostasis member 1224 may include one or more tissue contacting surfaces 1226 that are non-planar such as, for example, tissue contacting surfaces 1226 that are concave or convex in configuration. It is also envisioned that the tissue contacting surfaces 1226 may have an angled, stepped, or any other such configuration that allows the hemostasis member 1224 to vary in height. For example, the hemostasis member 1224 can have a lesser height at a distal end of the jaws 1010, 1012 (FIG. 1), and a greater height at a proximal end of the jaws, which may be useful in accommodating differences in tissue thickness. In other embodiments, the hemostasis member 1224 may include portions that vary in compressibility so as to apply more pressure to tissue in some regions of the hemostasis member 1224, and less pressure to tissue in other regions of the hemostasis member 1224. For example, portions of the hemostasis member can be made from a material that has different compressibility as compared to other portions.

By including a hemostasis member 1224 with tissue contacting surfaces 1226 that vary in height to define varying tissue gaps, and by configuring the hemostasis member 1224 such that the smallest tissue gap, i.e., the tissue gap "$G_A$" (FIG. 6), is nearest the slot 1212, and the largest tissue gap, i.e., the tissue gap "$G_C$" (FIG. 6), is furthest from the slot 1212, a greater range of tissue thickness can be effectively fastened. By including a hemostasis member 1224 with tissue contacting surfaces 1226 that vary in height, a single surgical fastener cartridge 1200 (FIG. 3) can be used to fasten tissue of varying thickness.

In the embodiment of the hemostasis member 1224 seen in FIGS. 3 and 6, the respective heights "$H_A$," "$H_B$," "$H_C$" of the inner, intermediate, and outer tissue contacting surfaces $1226_A$, $1226_B$, $1226_C$ remain substantially constant along the length of the surgical fastener cartridge 1200 (FIG. 3). Consequently, the respective inner, intermediate, and outer tissue contacting surfaces $1226_A$, $1226_B$, $1226_C$ of the hemostasis member 1224 and the tissue contacting surface 1102 of the anvil respectively define tissue gaps "$G_A$," "$G_B$," "$G_C$" that also remain substantially constant along the length of the surgical fastener cartridge 1200. As such, the compressive force applied to tissue positioned within the tissue gaps "$G_A$," "$G_B$," "$G_C$" upon approximation of the respective first and second jaws 1010, 1012 (FIG. 1) of the tool assembly 1006 will be substantially equivalent at the proximal and distal ends of the tool assembly 1006.

Figure 6A:
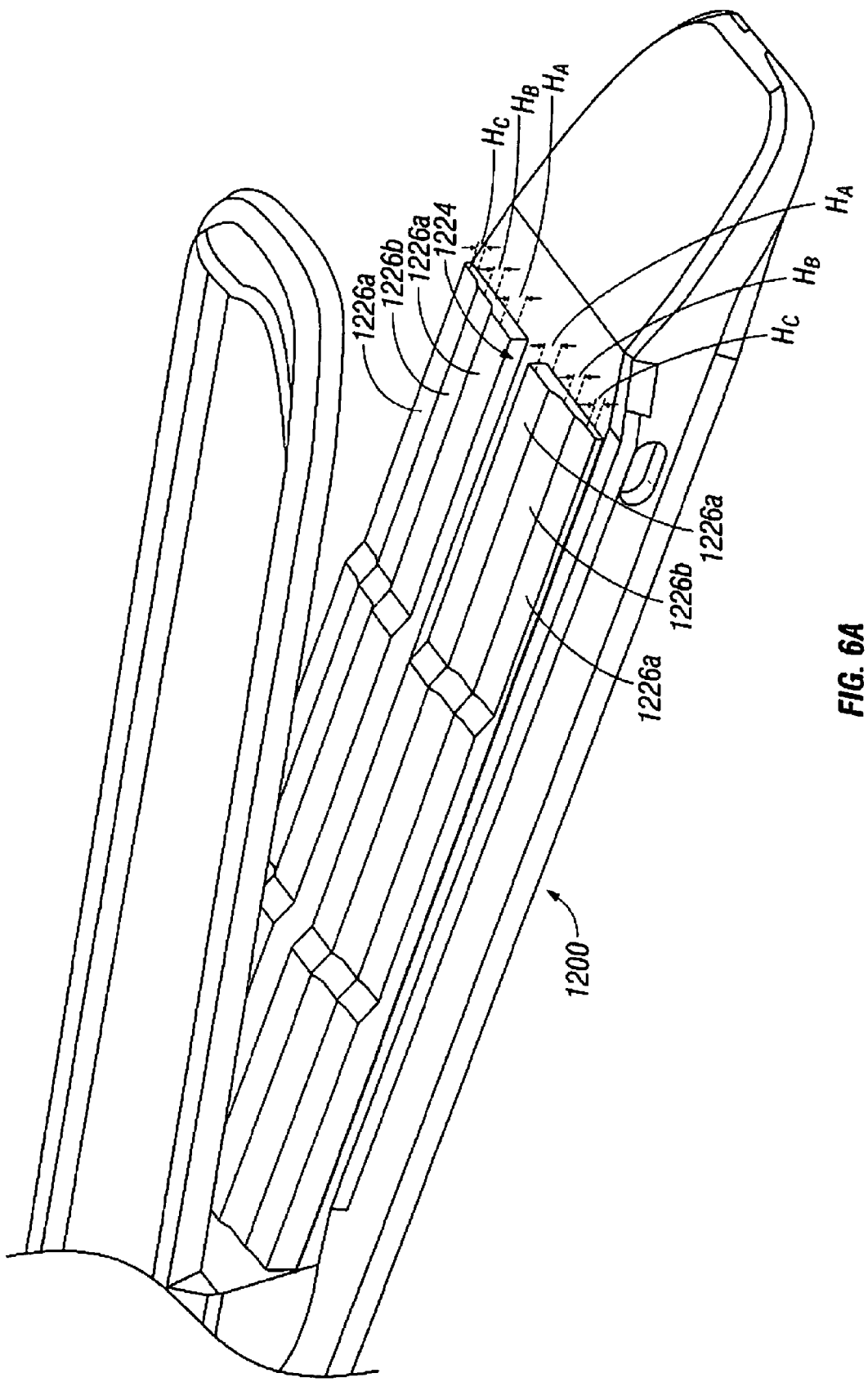
FIGS. 6A-6B are partial, perspective views of the tool assembly seen in FIG. 1 illustrating alternative embodiments of a hemostasis member according to the principles of the present disclosure.
Figure 6B:
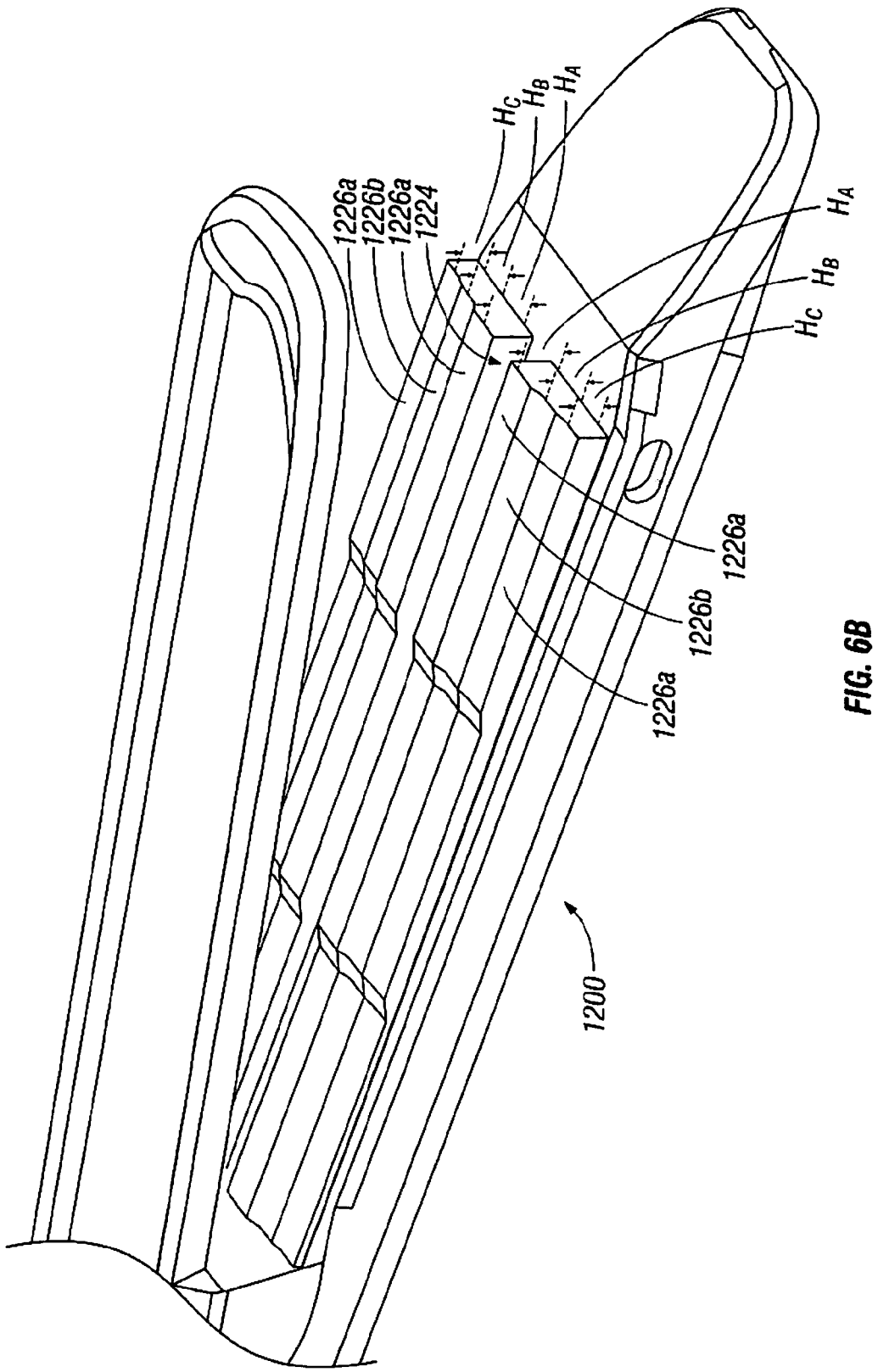

In alternative embodiments of the hemostasis member 1224, however, the respective heights "$H_A$," "$H_B$," "$H_C$" of the respective inner, intermediate, and outer tissue contacting surfaces $1226_A$, $1226_B$, $1226_C$ may vary along the length of the surgical fastener cartridge 1200, as illustrated in FIGS. 6A and 6B, such that the tissue gaps "$G_A$," "$G_B$," "Ge" (FIG. 6) also vary. By varying the respective heights "$H_A$," "$H_B$," "$H_C$" of the respective inner, intermediate, and outer tissue contacting surfaces $1226_A$, $1226_B$, $1226_C$ and the tissue gaps "$G_A$," "$G_B$," "$G_C$," the compressive force applied to the tissue can be increased or decreased along the length of the tool assembly 1006 (FIG. 1) such that the compressive force applied at one end may differ from that applied at the other end. Alternatively, the hemostasis member 1224 may have a single tissue contacting surface 1226 that varies in height at a distal portion, as compared to a more proximal portion, with an angled or stepped configuration.

While the anvil 1100 (FIGS. 1, 3), the surgical fastener cartridge 1200 (FIGS. 1, 3), and the various embodiments thereof described herein above have been discussed in connection with a plurality of substantially uniform surgical fasteners 100 (FIG. 2), in alternative embodiments of the present disclosure, the anvil 1100 and the surgical fastener cartridge 1200 may be adapted for use with a plurality of surgical fasteners having varying dimensions or configurations. For example, with reference to FIGS. 3 and 6, the pockets 1104 formed in the anvil 1100 and/or the retention slots 1214 formed in the surgical fastener cartridge 1200 may be configured and dimensioned to accommodate surgical fasteners having varying pre-formed heights "H" (FIG. 2).

Additionally, although each embodiment of the anvil 1100 (FIGS. 1, 3) and the surgical fastener cartridge 1200 (FIGS. 1, 3) discussed herein above has been described as including corresponding slots 1110, 1212, respectively, that are configured and dimensioned to accommodate movement of the knife 1111 (FIG. 3) subsequent to the fastening of tissue, the present disclosure also contemplates embodiments of the anvil 1100 and the surgical fastener cartridge 1200 that do not include such slots. In these embodiments, the tissue would be initially fastened and then severed subsequently thereafter, e.g., through the employ of a scalpel.

Referring now to FIGS. 1-6, a method of fastening tissue with the surgical fastener applying apparatus 1000 will be discussed. The surgical fastener applying apparatus 1000 is approximated and fired similarly to, and in accordance with other known surgical fastener applying apparatus, for example, the surgical fastener applying apparatus 1000 disclosed in commonly assigned U.S. Pat. No. 5,865,361, which is currently assigned to Tyco Healthcare Group LP, the disclosure of which is hereby incorporated by reference herein in its entirety.

As seen in FIG. 1, the handle assembly 1002 includes a movable handle member 1003$_A$. The movable handle 1003$_A$ is operatively connected to an actuation shaft, which receives the proximal end of a control rod such that linear advancement of the actuation shaft causes corresponding linear advancement of the control rod. An axial drive assembly is also provided that is engagable with the control rod. More specifically, the axial drive assembly includes an elongated drive beam 1113 with a distal end that supports the knife blade 1111 (FIG. 3) that is configured and dimensioned for engagement with the control rod. As seen in FIG. 3, the knife 1111 is positioned to translate behind the sled 1220. The drive beam 1113 travels in the slot 1110 in the anvil 1100 and the slot 1212 in the cartridge body 1202. An upper flange 1113$_A$ engages the anvil 1100 (FIG. 3), and a lower flange 1113$_B$ engages channel 1209 to close the jaws of the surgical fastener applying apparatus.

After the surgical fastener applying apparatus 1000 (FIG. 1) is manipulated such that the target tissue is disposed between the open jaws 1010, 1012 of the tool assembly 1006, the jaws 1010, 1012 are approximated using the handle assembly 1002 to clamp the target tissue therebetween and apply a compressive force thereto. Specifically, manipulation of the movable handle 1003$_A$ advances the actuation shaft to effectuate corresponding advancement of the control rod. In particular embodiments, the actuation shaft includes a toothed rack defined thereon, and the movable handle 1003$_A$ has a ratcheting pawl mounted thereto for incrementally engaging and advancing the actuation shaft. The pawl may be mounted on a pivot pin and a coiled torsion spring that biases the pawl into engagement with the toothed rack. The control rod is connected at its distal end to the drive assembly, which includes the aforementioned drive beam 1113, such that distal movement of control rod effects distal movement of the drive beam 1113, which in turn, forces the anvil 1100 towards the cartridge 1200. Specifically, the control rod advances the drive beam 1113 distally such that the upper and lower flanges 1113$_A$, 1113$_B$ engage the anvil 1100 and the channel 1209, respectively.

With the tissue securely clamped between the jaws 1010, 1012, the surgical fastener applying apparatus 1000 is then fired to eject the surgical fasteners by once again actuating the movable handle 1003$_A$. To fire the surgical fastener applying apparatus 1000, the movable handle 1003$_A$ is again manipulated to cause advancement of the drive assembly, which causes the sled 1220 (FIG. 3) to traverse the cartridge body 1202 and engage the pushers 1218 (FIG. 3) to thereby eject the plurality of surgical fasteners 100 from the surgical fastener cartridge 1200. Specifically, angled leading surfaces of the sled 1220 sequentially contact the pushers 1218 at cam surfaces included thereon as the sled translates. The interaction between the leading surfaces of the sled 1220 and the cam surfaces of the pushers 1218 urges the pushers 1218 towards the top wall 1210 of the cartridge body 1202. Sequential firing of the surgical fasteners 100 continues until the sled 1220 is advanced to the distal end of the cartridge 1200, at which time all of the surgical fasteners 100 housed the cartridge 1200 will have been ejected.

The plurality of surgical fasteners 100 pass through the retention slots 1214 (FIGS. 3, 6) formed in the top wall 1210 of the surgical fastener cartridge 1200, and thereafter, through the hemostasis member 1224 and the tissue. After passing through the tissue, the plurality of surgical fasteners 100 are formed through engagement with the pockets 1104 (FIGS. 3, 4, 6) defined in the tissue contacting surface 1102 of the anvil 1100 to achieve, for example, the standard "B" shaped configuration (FIG. 7). Upon formation within the tissue, the plurality of surgical fasteners 100 act to maintain the compressive force applied thereto by the hemostasis member 1224 during clamping of the respective first and second jaws 1010, 1012 (FIG. 1) of the tool assembly 1006. Accordingly, the flow of blood through the tissue immediately adjacent and surrounding the cut-line will be less than the flow of blood through the tissue spaced laterally therefrom. More specifically, the tissue at the outer rows 1222C will be compressed less than the tissue at rows 1222B, and the tissue at rows 1222B will be compressed less than the tissue at rows 1222A. The flow of blood through the tissue surrounding the surgical fasteners 100 in rows 1222C will be less restricted when compared to the flow of blood through the tissue surrounding the surgical fasteners 100 in rows 1222B, and the flow of blood through the tissue surrounding the surgical fasteners 100 in rows 1222B will be less restricted when compared to the flow of blood through the tissue surrounding the surgical fasteners 100 in rows 1222A.

The configuration of the hemostasis member 1224, e.g., the respective heights "H$_B$", "H$_C$" of the intermediate and outer tissue contacting surfaces 1226$_B$, 1226$_C$, and the thickness of the tissue, is such that the flow of blood through the tissue surrounding the surgical fasteners 100 in rows 1222$_C$, 1222$_B$ is limited, but not so restricted as to necrose the tissue, thereby facilitating hemostasis. The greater height "H$_A$" of the inner tissue contacting surface 1226$_A$, however, is such that the flow of blood through the tissue surrounding the surgical fasteners 100 at row 1222A is substantially, if not completely restricted, thereby further facilitating and effectuating hemostasis.

While the surgical fastener applying apparatus 1000 has been discussed, and illustrated, in connection with the tool assembly 1006 (FIG. 1), which is adapted for use in laparoscopic procedures for performing surgical anastomotic fastening of tissue, the disclosed hemostasis member 1224 may be adapted for use with any surgical instrument suitable for the intended purpose of applying the plurality of surgical fasteners 100 (FIGS. 2, 3) to a section of tissue, and thereafter severing the tissue along a cut-line.

Figure 10:
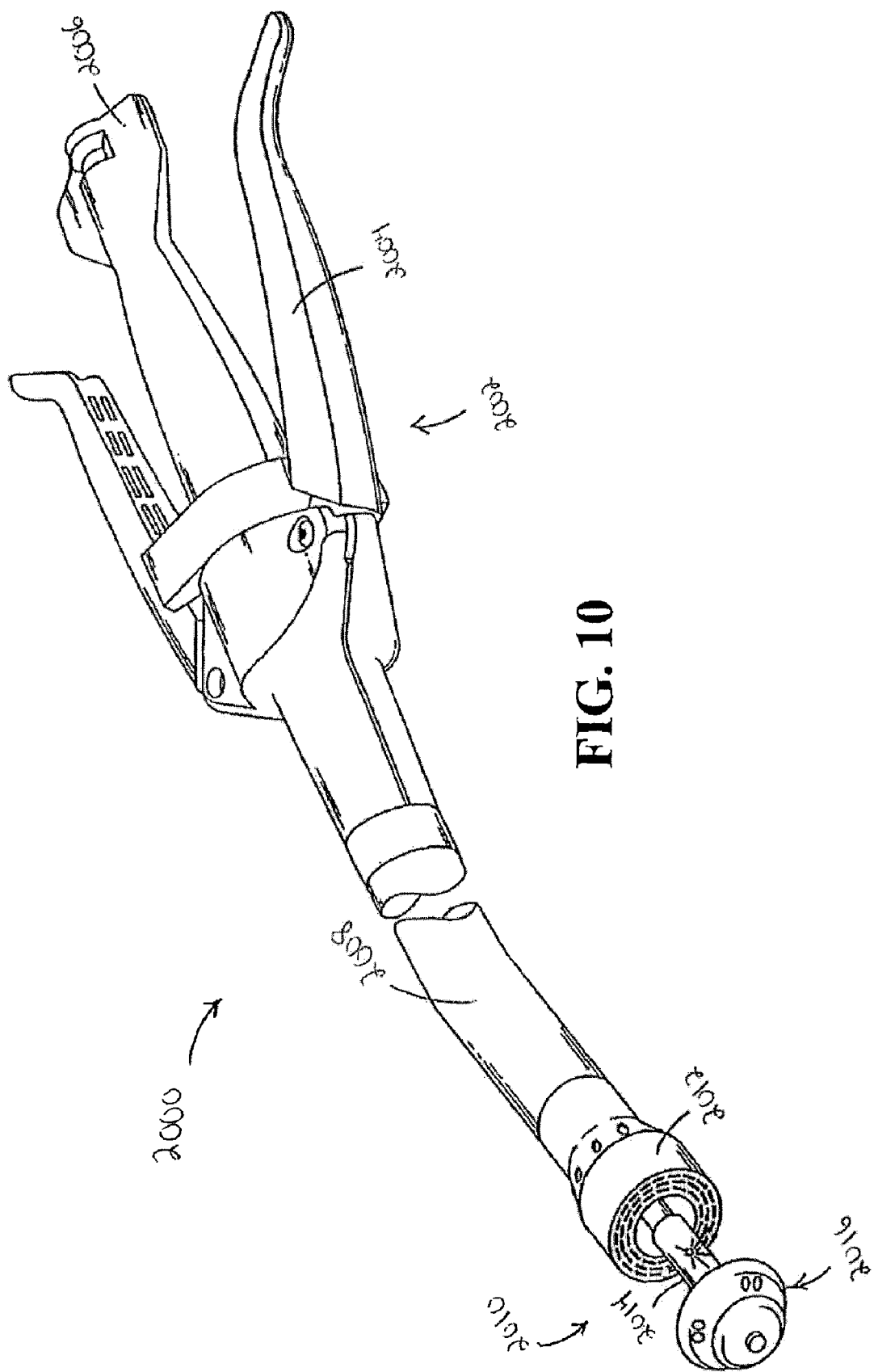
FIG. 10 illustrates an end-to-end anastomosis device for use with alternative embodiments of the anvil and the surgical fastener cartridge seen in FIG. 3.

For example, the hemostasis member 1224 may be adapted for use with an end-to-end anastomosis (EEA) apparatus 2000 (FIG. 10), such as that disclosed in commonly assigned U.S. Pat. No. 7,455,676, currently assigned to Tyco Healthcare Group LP, the contents of which are hereby incorporated by reference herein in its entirety. The EEA apparatus 2000 includes a handle assembly 2002 having at least one pivotable actuating handle member 2004, and advancing means 2006. Extending from handle assembly 2002, there is provided a tubular body portion 2008 that terminates in a fastener ejection (tool) assembly 2010 having a circular fastener cartridge 2012 that is configured and dimensioned to retain a plurality of surgical fasteners therein. Accordingly, it is envisioned that the hemostasis member 1224 may be arcuate, or generally donut-shaped in configuration, with thicker portions positioned along an inner edge of the hemostasis member 1224, i.e., closer to the anvil shaft 2014. The anvil shaft 2014 operatively couples an anvil assembly 2016 to the handle assembly 2002 such that the anvil assembly 2016 is repositionable from a location where it is in close cooperative alignment with the fastener cartridge 2012 to a location where it is spaced apart from the fastener staple cartridge 2012.

The tool assembly 2010 includes a fastener ejection member that is positioned within the fastener cartridge 2012. The fastener ejection member includes a distal portion defining concentric rings of peripherally spaced staple pushers that are received within a respective staple retention slot to eject the surgical fasteners from the fastener cartridge 2012. The fastener ejection member is configured and dimensioned to be contacted by a distal end of a driver tube that is operatively connected to the advancing means 2006 through the body portion 2008 such that manipulation of the advancing means effectuates advancement of the driver tube to force the staple pushers into engagement with the plurality of surgical fasteners retained with in the fastener cartridge 2012 to causes ejection thereof.

Figure 11:
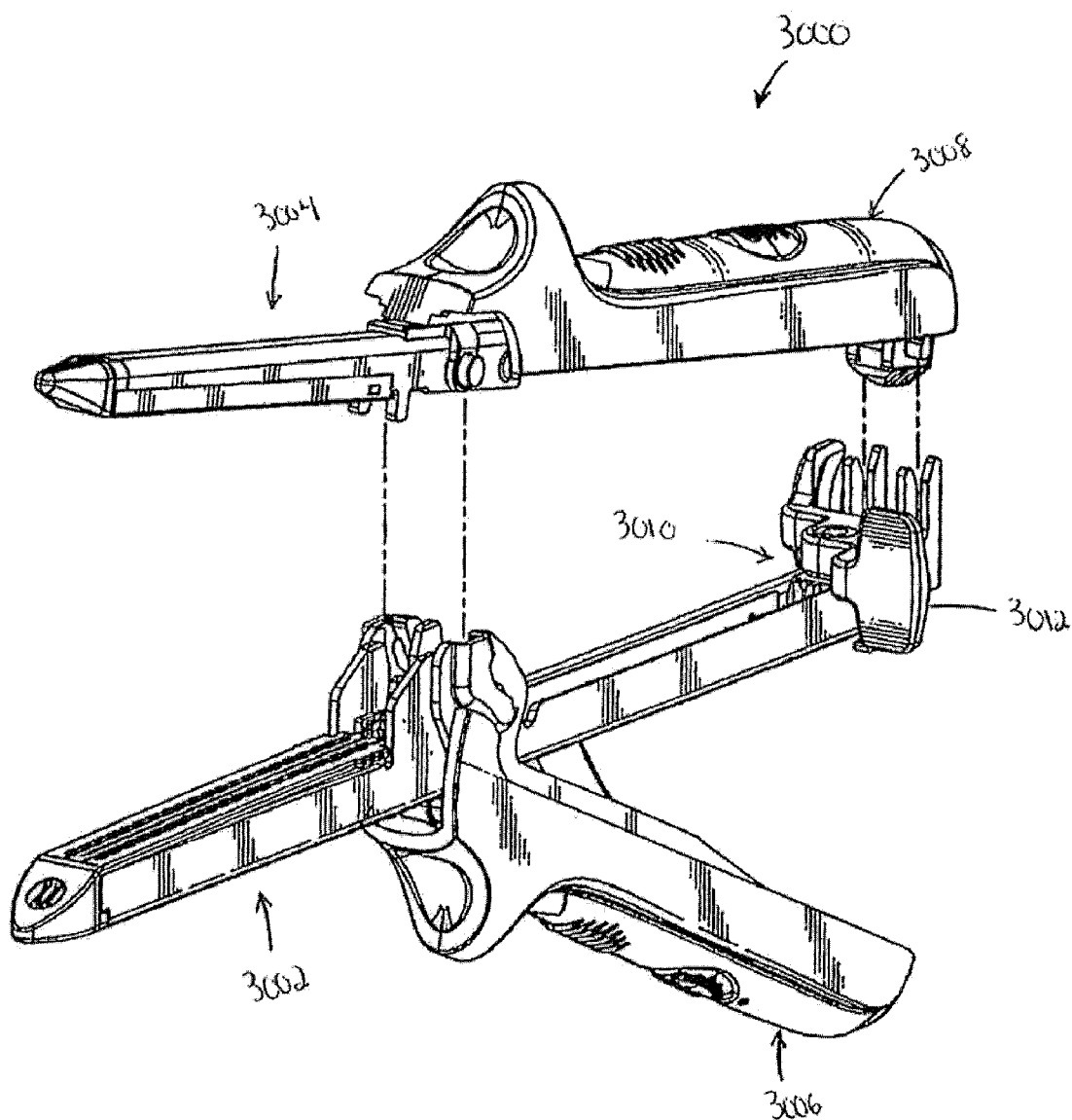
FIG. 11 illustrates a surgical fastener applying instrument in accordance with a further embodiment of the present disclosure.

The hemostasis member 1224 may also be adapted for use with a surgical stapling apparatus 3000 (FIG. 11), such as that disclosed in commonly assigned U.S. Pat. No. 7,334,717, currently assigned to Tyco Healthcare Group LP, the contents of which are hereby incorporated by reference herein in its entirety. The surgical stapling apparatus 3000 includes a cartridge receiving half-section 3002, which accommodates a plurality of surgical fasteners, and an anvil half-section 3004. The half-sections 3002, 3004 are pivotally connected via handles 3006, 3008 for approximation during use.

Following approximation of the half-sections 3002, 3004, the surgical fastener applying apparatus 3000 is fired by driving a firing slide 3010 distally through the advancement of a firing lever 3012. Distal movement of the firing slide 3010 causes a plurality of cam bars to engage camming surfaces that interact with a plurality of pushers to expel the plurality of surgical fasteners from the cartridge receiving half-section 3002. The surgical fasteners are positioned on either side of a track which guides a knife during longitudinal movement to thereby sever tissue along a cut-line.

Figure 12:
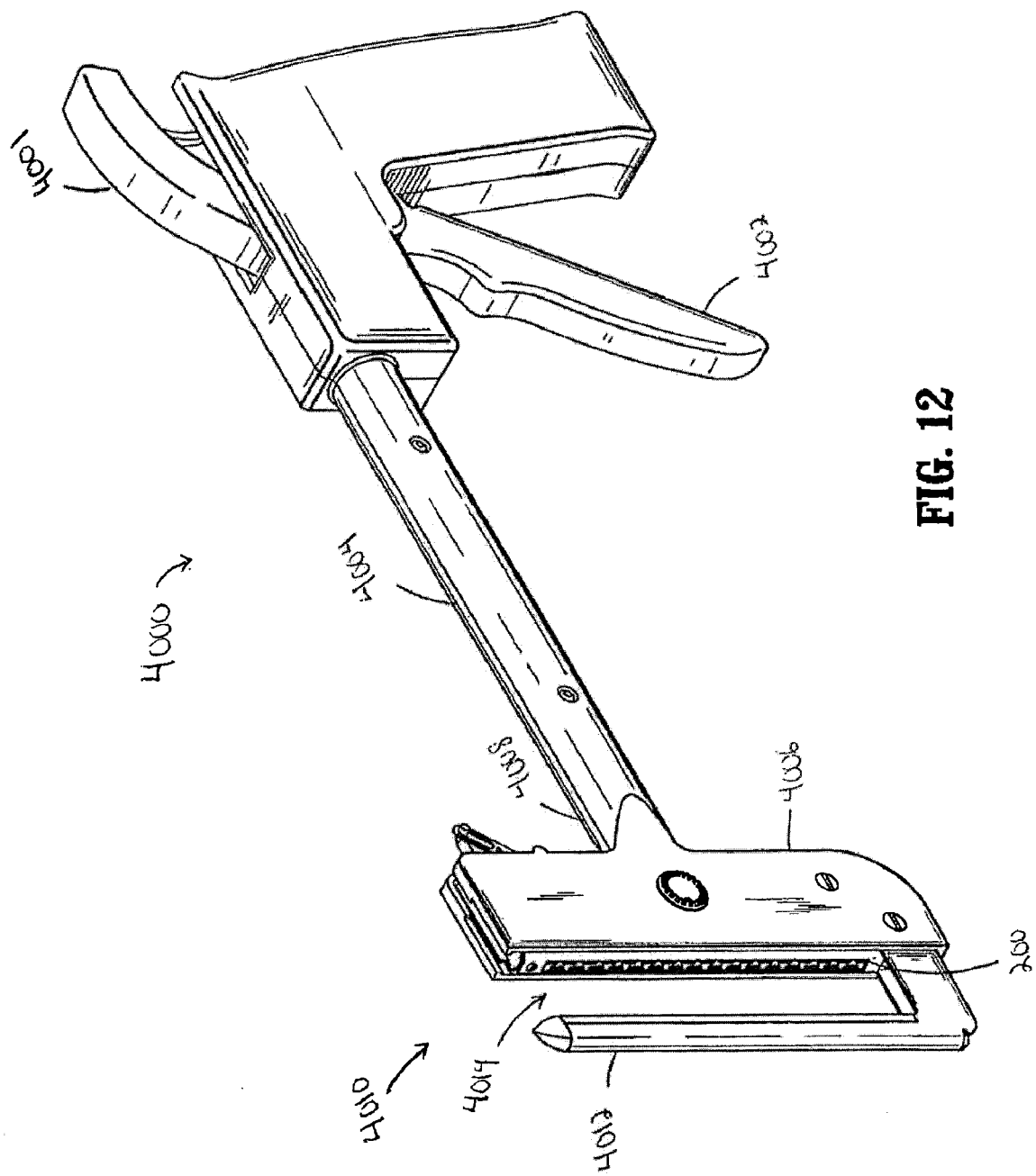
FIG. 12 illustrates a transverse anastomosis fastener applying instrument in accordance with another embodiment of the present disclosure.

The hemostasis member 1224 may also be adapted for use with a transverse anastomosis fastening instrument 4000 (FIG. 12), such as that disclosed in commonly owned U.S. Pat. No. 5,964,394, currently assigned to United States Surgical Corporation, the contents of which are hereby incorporated by reference herein in its entirety. The surgical fastener applying apparatus 4000 includes an approximation lever 4001, a movable handle 4002, an elongated portion 4004 that extends distally from the handle 4002, and an arm 4006 that extends from a distal end 4008 of the elongated portion 4004. The surgical fastener applying apparatus 4000 further includes a tool assembly 4010 that includes an anvil 4012 that is orthogonally affixed to the arm 4006, and a surgical fastener cartridge receiver 4014 that is operatively coupled to the distal end 4008 of the elongated portion 4004 for retention of the surgical fastener cartridge 200.

Prior to firing of the surgical fastener applying apparatus 4000, the approximation lever 4001 is actuated to distally advance a drive member that is operatively connected to the surgical fastener cartridge 200 to move the surgical fastener cartridge 200 towards the anvil 4012, which remains stationary, and capture tissue therebetween. Thereafter, the handle 4002 is moved to advance a pusher bar distally through the elongated portion 4004 to cause corresponding movement of a head portion included at the distal end of the pusher bar. The head portion includes a plurality of fingers extending distally therefrom that are configured and dimensioned to engage the cartridge assembly to thereby discharge the plurality of surgical fasteners retained therein. Upon discharge, the surgical fasteners are driven through the tissue and into the anvil 4012 for formation.

It is also envisioned that the tool assembly 1006 (FIG. 1) may also be adapted for use with any of the other surgical fastener applying apparatus discussed in commonly owned U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, the disclosures of which are hereby incorporated by reference herein in their entirety.

In certain embodiments of the present disclosure, it is envisioned that the disclosed surgical fastener applying apparatus may include a plurality of cam bars for interacting with the pushers to deploy the surgical fasteners. For example, the apparatus disclosed in commonly owned U.S. Pat. No. 5,318,221, the disclosure of which is hereby incorporated by reference herein in its entirety, includes a cam bar adapter that holds a plurality of cam bars and a knife, as well as a channel that is advanced through operation of the handle of the apparatus, which drives the cam bars and knife forward. To clamp the anvil and the surgical fastener cartridge together, the apparatus further includes a clamp tube that is movable to surround the proximal end of the anvil.

As another example, the apparatus disclosed in U.S. Pat. No. 5,782,396, the disclosure of which is hereby incorporated by reference herein in its entirety, includes an actuation sled and an elongated drive beam that is advanced distally through operation of the handle of the apparatus, driving the actuation sled forward. In this apparatus, the distal end of the drive beam engages the anvil and the channel that supports the surgical fastener cartridge as the drive beam travels distally to deploy the staples and clamp the anvil and surgical fastener cartridge together.

Figure 13:
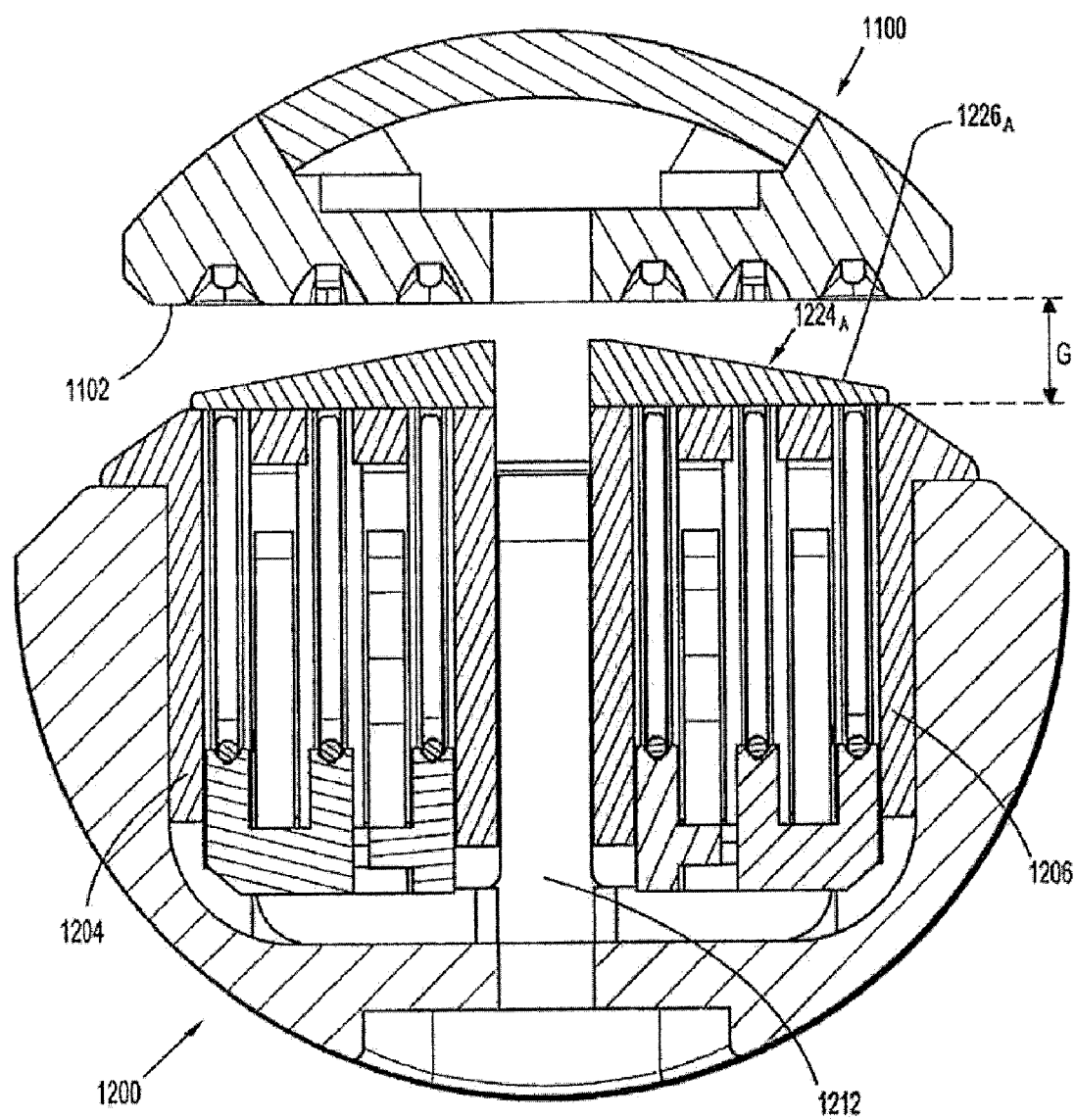
FIG. 13 is a lateral, cross-sectional view of the tool assembly seen in FIG. 1 taken through the pockets formed in the anvil and retention slots formed in the surgical fastener cartridge in accordance with an alternative embodiment of the present disclosure.

Referring now to FIG. 13, an alternative embodiment of the hemostasis member, referred to generally by the reference character 1224$_A$, will be discussed in connection with the aforedescribed surgical fastener cartridge 1200 and the anvil 1100. The hemostasis member 1224$_A$ is substantially identical to the hemostasis member 1224 that was discussed above in connection with FIGS. 3 and 6, but for the tapered configuration thereof. While illustrated as substantially linear in FIG. 13, alternatively, it is also envisioned that the taper defined by the hemostasis member 1224$_A$ may be partially, or completely, arcuate. The hemostasis member may be a bio-absorbable or non-absorbable material suitable for implantation in the body and configured as a mesh, pad of material, composite materials, materials including fibers, collagen or other materials derived from natural tissue, and other materials for surgical implantation. The hemostasis member may comprise a known surgical stapling buttress, pledget, or tissue support, and may be formed from, or include, a hemostat, medicament, coagulant, adhesive, or sealant. The materials described in U.S. Patent Application Publication No. 2007-0203510 A1, published Aug. 30, 2007, the disclosure of which is hereby incorporated by reference herein, may be used to form the hemostasis member.

The configuration of the hemostasis member applies different pressure to tissue, depending upon the location of the tissue with respect to the hemostasis member. The tapered configuration of the hemostasis member 1224$_A$ decreases in height from the slot 1212 extending through the hemostasis member 1224$_A$ towards the outer walls 1204, 1206 of the cartridge body 1202. Accordingly, the tissue gap "G" defined between the tissue contacting surface 1226$_A$ of the hemostasis member 1224$_A$ and the tissue contacting surface 1102 of the anvil 1100 is at a minimum immediately adjacent the slot 1212, and at a maximum adjacent the outer walls 1204, 1206. As such, the hemostasis member 1224$_A$ will apply a compressive force to the tissue that gradually decreases as the distance from the slot 1212 is increased such that the flow of blood through tissue immediately adjacent and surrounding the cut-line will be less than the flow of blood through the tissue further removed therefrom.

The above description, disclosure, and figures should not be construed as limiting, but merely as exemplary of particular embodiments. It is to be understood, therefore, that the disclosure is not limited to the precise embodiments described, and that various other changes and modifications may be effected by one skilled in the art without departing from the scope or spirit of the disclosure. Additionally, those skilled in the art will appreciate that the elements and features illustrated or described in connection with one embodiment can be combined with those of another, and that such modifications and variations are also intended to be included within the scope of the present disclosure.

What is claimed is:

1. A surgical fastener applying apparatus, comprising:
a first jaw having proximal and distal ends and including an anvil member, the anvil member extending along a longitudinal axis and including a tissue contacting surface;
a second jaw having proximal and distal ends movably coupled to the first jaw and including a cartridge member; and
a hemostasis member positioned between the first jaw and the second jaw, the hemostasis member having a stepped profile configured and dimensioned to apply at least two different compressive forces to tissue during approximation of the first and second jaws, the hemostasis member having a height that is varied along the longitudinal axis such that the compressive forces are varied along the longitudinal axis.

2. The surgical fastener applying apparatus of claim 1, wherein the hemostasis member is configured and dimensioned such that the compressive forces are also varied along an axis transverse to the longitudinal axis.

3. The surgical fastener applying apparatus of claim 2, wherein the hemostasis member is configured and dimensioned such that the compressive forces applied to the tissue decreases outwardly relative to a centerline of the cartridge member such that blood flow through the tissue nearer to the centerline of the cartridge member is less than blood flow through the tissue further from the centerline of the cartridge member.

4. The surgical fastener applying apparatus of claim 1, wherein the hemostasis member is configured and dimensioned such that the compressive forces applied to the tissue decrease in a proximal direction along the longitudinal axis such that blood flow through the tissue nearer to the distal ends of the anvil member and the cartridge member is less than blood flow through the tissue nearer to the proximal ends of the anvil member and the cartridge member.

5. The surgical fastener applying apparatus of claim 1, wherein the hemostasis member is configured and dimensioned such that the compressive forces applied to the tissue decrease in a distal direction along the longitudinal axis such that blood flow through tissue nearer to the proximal ends of the anvil member and the cartridge member is less than blood flow through tissue nearer to the distal ends of the anvil member and the cartridge member.

6. The surgical fastener applying apparatus of claim 2, wherein the stepped profile of the hemostasis member defines a first tissue contacting surface and a second tissue contacting surface, the second tissue contacting surface being positioned outwardly of the first tissue contacting surface relative to the longitudinal axis, the first tissue contacting surface defining a first gap with the tissue contacting surface of the anvil member and the second tissue contacting surface defining a second gap with the tissue contacting surface of the anvil member, the second gap being larger than the first gap.

7. The surgical fastener applying apparatus of claim 6, wherein the first and second tissue contacting surfaces are generally planar in configuration.

8. The surgical fastener applying apparatus of claim 6, wherein the first tissue contacting surface is connected to the second tissue contacting surface via a first wall surface, the first wall surface having a generally tapered configuration.

9. The surgical fastener applying apparatus of claim 6, wherein the stepped profile of the hemostasis member further defines a third tissue contacting surface positioned outwardly of the second tissue contacting surface relative to the longitudinal axis, the third tissue contacting surface defining a third gap with the tissue contacting surface of the anvil member that is larger than the second gap.

10. The surgical fastener applying apparatus of claim 9, wherein the second tissue contacting surface is connected to the third tissue contacting surface via a second wall surface, the second wall surface having a generally tapered configuration.

11. The surgical fastener applying apparatus of claim 1, further including a plurality of surgical fasteners positioned within the cartridge member, each surgical fastener having a substantially equivalent height.

12. The surgical fastener applying apparatus of claim 1, wherein the hemostasis member is formed of a substantially resilient material to support layers of tissue positioned between the first and second jaws.

13. The surgical fastener applying apparatus of claim 1, wherein the hemostasis member is fixedly secured to the cartridge member.

14. The surgical fastener applying apparatus of claim 1, wherein the hemostasis member is releasably secured to the cartridge member.

15. The surgical fastener applying apparatus of claim 1, wherein the anvil member includes a plurality of pockets formed therein, each pocket includes a forming surface extending into the tissue contacting surface of the anvil member to define a substantially equivalent depth.

16. A hemostasis member for use with a surgical fastener applying apparatus including an anvil and a cartridge having a plurality of surgical fasteners arranged in at least one row, the hemostasis member being shaped and configured to overlie the at least one row of surgical fasteners, the hemostasis member having a height that is varied along a longitudinal axis of the surgical fastener applying apparatus such that at least two different compressive forces are applied to tissue at locations along the longitudinal axis during approximation of the anvil member and the cartridge member.

17. The hemostasis member of claim 16, wherein the hemostasis member is configured and dimensioned such that the compressive force is also varied along an axis extending in transverse relation to the longitudinal axis.

18. The hemostasis member of claim 17, wherein the hemostasis member is configured and dimensioned such that the compressive force applied to the tissue decreases outwardly relative to a centerline of the cartridge member such that blood flow through the tissue nearer to the centerline of the cartridge member is less than blood flow through the tissue further from the centerline of the cartridge member.

* * * * *